United States Patent
Ohtani et al.

(10) Patent No.: US 10,926,488 B2
(45) Date of Patent: Feb. 23, 2021

(54) COMPOSITE MATERIAL, METHOD FOR MANUFACTURING COMPOSITE MATERIAL, AND METHOD FOR MANUFACTURING MOLDED ARTICLE

(71) Applicant: Mitsubishi Gas Chemical Company, Inc., Tokyo (JP)

(72) Inventors: Akio Ohtani, Gifu (JP); Asami Nakai, Gifu (JP); Masataka Kaji, Ishikawa (JP); Mitsuro Takagi, Ishikawa (JP); Nobuhiko Matsumoto, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 350 days.

(21) Appl. No.: 15/563,922

(22) PCT Filed: Apr. 1, 2016

(86) PCT No.: PCT/JP2016/060891
§ 371 (c)(1),
(2) Date: Oct. 2, 2017

(87) PCT Pub. No.: WO2016/159340
PCT Pub. Date: Oct. 6, 2016

(65) Prior Publication Data
US 2018/0126674 A1    May 10, 2018

(30) Foreign Application Priority Data

Apr. 3, 2015  (JP) .............................. JP2015-077031
Nov. 24, 2015  (JP) .............................. JP2015-228440

(51) Int. Cl.
*B29C 70/22*    (2006.01)
*B29C 70/20*    (2006.01)
(Continued)

(52) U.S. Cl.
CPC .......... *B29C 70/226* (2013.01); *A61F 5/0102* (2013.01); *B29B 11/16* (2013.01);
(Continued)

(58) Field of Classification Search
None
See application file for complete search history.

(56) References Cited

U.S. PATENT DOCUMENTS 6,294,036 B1 * 9/2001 Loubinoux ............... B32B 5/26
                                                          156/181
2003/0199667 A1 * 10/2003 Maruo ................... C08G 69/02
                                                          528/310

(Continued)

FOREIGN PATENT DOCUMENTS

CN    102770480 A    11/2012
CN    103397429 A    11/2013
(Continued)

OTHER PUBLICATIONS

Machine translation of CN102770480, Akira et al. (Year: 2012).*
(Continued)

*Primary Examiner* — Shawn Mckinnon
(74) *Attorney, Agent, or Firm* — Fitch, Even, Tabin & Flannery, LLP

(57) ABSTRACT

Provided is a composite material capable of keeping a good appearance even after heat processed, a method for manufacturing a composite material and a method for manufacturing a molded article. The composite material of the present invention contains a commingled yarn that contains a continuous reinforcing fiber (A) and a continuous thermoplastic resin fiber (B) as fiber components thereof; and a thermoplastic resin fiber (C) that keeps the commingled yarn in place, a thermoplastic resin that composes the thermoplastic resin fiber (C) having a melting point 15° C. or more
(Continued)

higher than the melting point of a thermoplastic resin that composes the continuous thermoplastic resin fiber (B).

15 Claims, 4 Drawing Sheets

(51) Int. Cl.
```
C08J 5/04      (2006.01)
A61F 5/01      (2006.01)
B29C 43/18     (2006.01)
B32B 5/02      (2006.01)
B32B 27/12     (2006.01)
B32B 27/28     (2006.01)
D02G 3/40      (2006.01)
B29B 11/16     (2006.01)
B29C 70/34     (2006.01)
B27N 3/12      (2006.01)
```
(52) U.S. Cl.
CPC ............ *B29C 43/18* (2013.01); *B29C 70/205* (2013.01); *B32B 5/02* (2013.01); *B32B 27/12* (2013.01); *B32B 27/281* (2013.01); *C08J 5/04* (2013.01); *C08J 5/047* (2013.01); *D02G 3/402* (2013.01); *B27N 3/12* (2013.01); *B29C 70/34* (2013.01); *B32B 2262/0269* (2013.01); *B32B 2262/101* (2013.01); *B32B 2262/106* (2013.01); *C08J 2377/06* (2013.01); *D10B 2505/02* (2013.01)

(56) References Cited

U.S. PATENT DOCUMENTS

| | | | |
|---|---|---|---|
| 2007/0072505 A1* | 3/2007 | Loubinoux | ............ D04H 5/03 442/366 |
| 2010/0318108 A1* | 12/2010 | Datta | ............ A61L 31/146 606/151 |
| 2011/0167545 A1* | 7/2011 | Garcia | ............ D04B 1/14 2/455 |
| 2012/0302118 A1 | 11/2012 | Kasuya et al. | |
| 2013/0123439 A1* | 5/2013 | Mitadera | ............ C08G 69/26 525/92 B |
| 2016/0010246 A1 | 1/2016 | Nakai et al. | |
| 2017/0260657 A1 | 9/2017 | Nakai et al. | |

FOREIGN PATENT DOCUMENTS

| | | |
|---|---|---|
| DE | 102010052078 A1 | 5/2012 |
| JP | H01-266231 A | 10/1989 |
| JP | H02-112916 A | 4/1990 |
| JP | H04-163002 A | 6/1992 |
| JP | H06-228837 A | 8/1994 |
| JP | H06-238014 A | 8/1994 |
| JP | 2009-019202 A | 1/2009 |
| JP | 2010-017934 A | 1/2010 |
| JP | 2011-207198 A | 10/2011 |
| JP | 2014-169411 A | 9/2014 |
| JP | 2014-173196 A | 9/2014 |
| JP | 2015-101794 A | 6/2015 |
| WO | 2015/157175 A1 | 10/2015 |
| WO | 2016/039242 A1 | 3/2016 |

OTHER PUBLICATIONS

Extended European Search Report issued in corresponding European Application No. 16773220.5 dated Nov. 2, 2018 (8 pages).
Office Action dated Apr. 25, 2019, in corresponding Chinese Patent Application No. 201680020135.1.
Office Action dated Jun. 4, 2019, in corresponding Taiwanese Patent Application No. 105110429.
Office Action dated Aug. 27, 2019, in corresponding Japanese Patent Application No. 2015-228440.
International Search Report for PCT/JP2016/060891 dated Jun. 21, 2016; English translation submitted herewith (6 pages).

* cited by examiner

[Fig. 1]
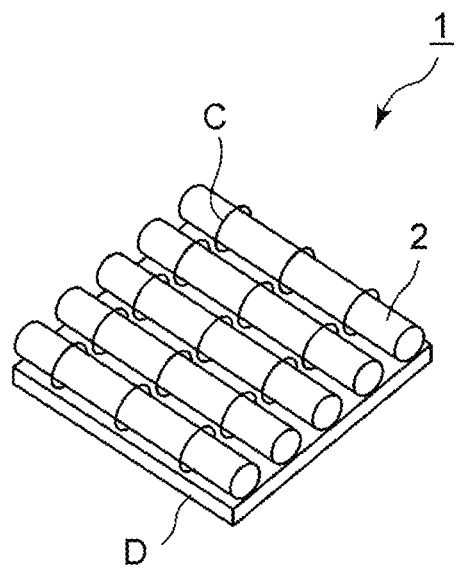
[Fig. 2]
(a)　　　　　　　　(b)　　　　　　　　(c)
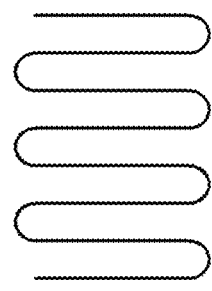 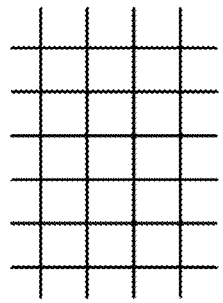 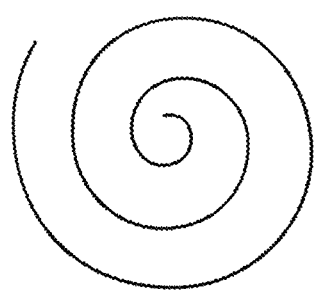

[Fig. 3]
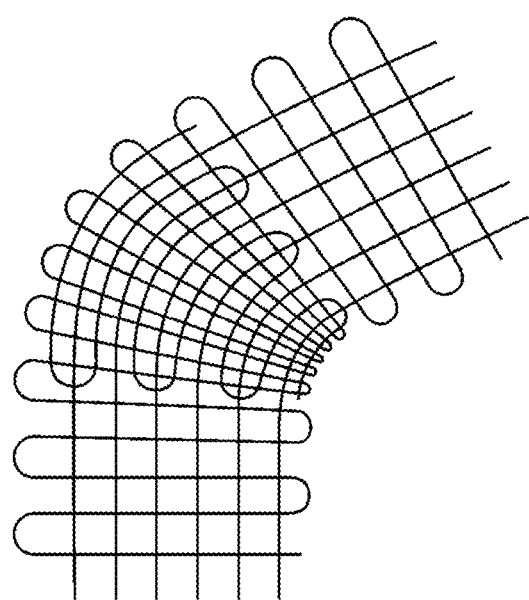
[Fig. 4]
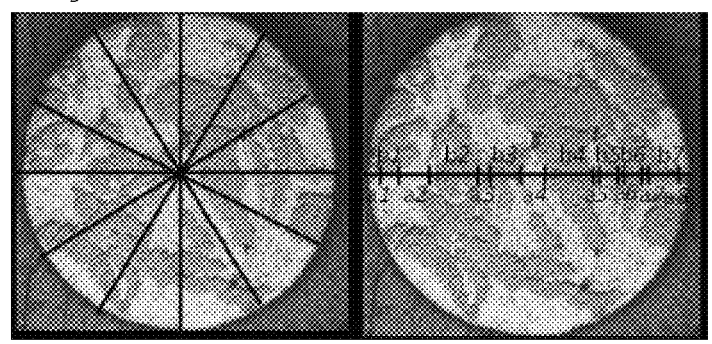

[Fig. 5]
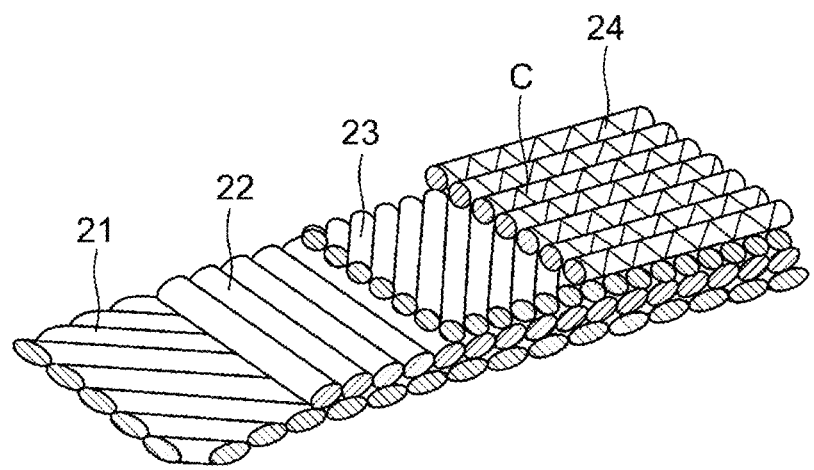
[Fig. 6]
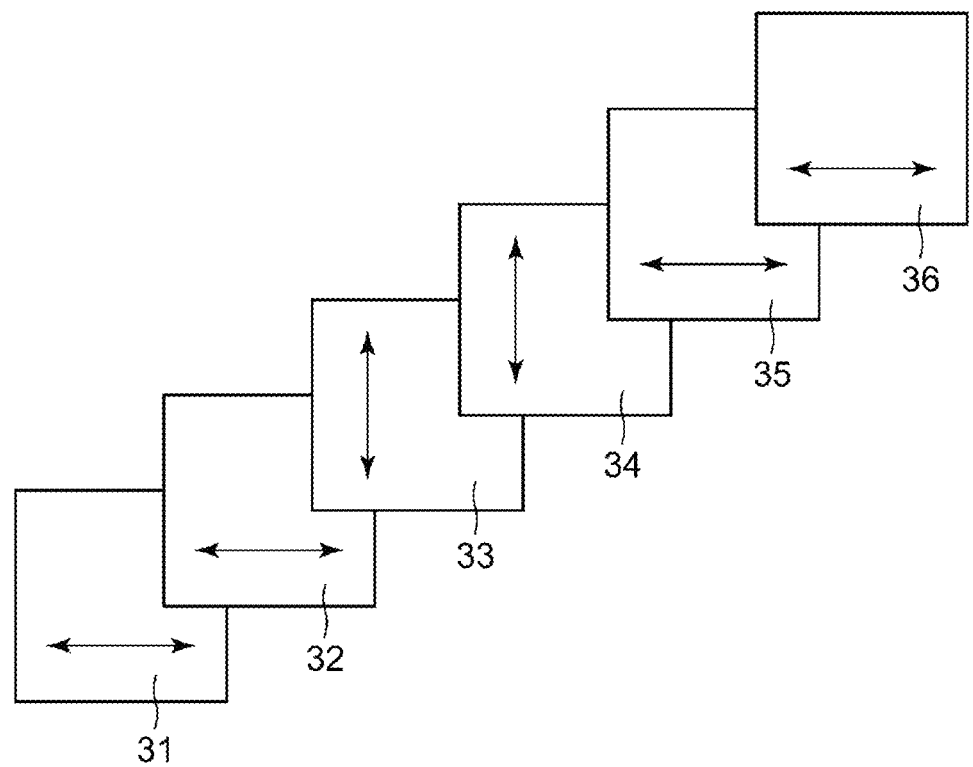

[Fig. 7]
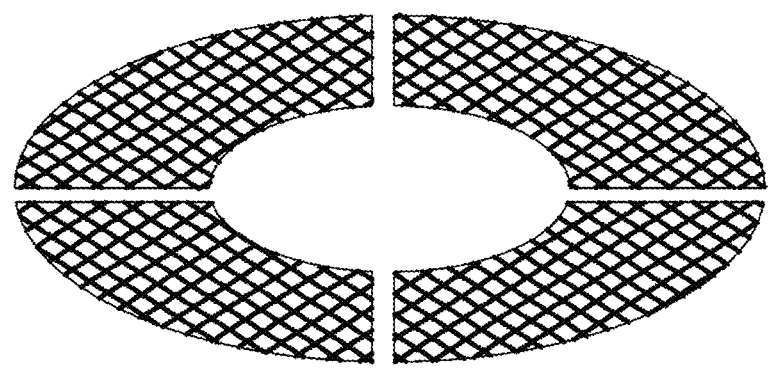

COMPOSITE MATERIAL, METHOD FOR MANUFACTURING COMPOSITE MATERIAL, AND METHOD FOR MANUFACTURING MOLDED ARTICLE

CROSS-REFERENCE TO RELATED APPLICATIONS

This application is a U.S. national phase application filed under 35 U.S.C. § 371 of International Application PCT/JP2016/060891, filed on Apr. 1, 2016, designating the United States, which claims priority from Japanese Application Number 2015-077031, filed Apr. 3, 2015, and Japanese Application Number 2015-228440, filed Nov. 24, 2015, which are each hereby incorporated herein by reference in their entirety.

FIELD OF THE INVENTION

This invention relates to a composite material, a method for manufacturing a composite material, and, a method for manufacturing a molded article using the composite material.

BACKGROUND OF THE INVENTION

In recent years, fiber reinforced thermoplastic resin material (fiber-reinforced thermoplastics, or FRP) that contains fiber and thermoplastic resin has attracted public attention (Patent Literatures 1 to 4). The FRP, featured by its light weight and high strength, has been used for miscellaneous applications.

As a representative example of the FRP, there is known a fiber reinforced thermoplastic resin material in which a thermoplastic resin impregnated into fibers. This sort of FRP is typically used as a prepreg, which is obtained by bonding, under heating, a plurality of fiber reinforced thermoplastic resin materials in which a thermoplastic resin impregnated into fibers. Such prepreg is further shaped by heating, depending on intended applications.

The present applicant has ever disclosed a commingled yarn whose fiber component is composed of a continuous thermoplastic resin fiber and a continuous reinforcing fiber.

CITATION LIST

Patent Literatures

[Patent Literature 1] JP-A-2011-207198
[Patent Literature 2] JP-A-2014-169411
[Patent Literature 3] JP-A-2010-17934
[Patent Literature 4] JP-A-2014-173196

SUMMARY OF THE INVENTION

Since the above-described commingled yarn, whose fiber component includes a continuous reinforcing fiber and a continuous thermoplastic resin fiber, has a form of thread, so that it would be beneficial to provide the yarn while kept in place typically in a sheet form. However, a composite material, having thereon the commingled yarn kept in place with some kind of fiber, may sometimes show degraded appearance after heat processed, since the continuous fiber is disordered and becomes more recognizable on the surface of a molded article.

It is therefore an object of this invention to solve the problem, and to provide a composite material capable of keeping a good appearance even after heat processed. Another object is to provide a method for manufacturing a composite material and a method for manufacturing a molded article.

Under such situation, the present inventors found after extensive investigations that the above problem can be solved by employing, as a fiber for keeping the commingled yarn in place, a resin fiber having a melting point higher than a melting point of a resin contained in the commingled yarn. The finding led us to complete this invention. The above-described problem was solved by a means <1>, and preferably by means <2> to <18>.

<1> A composite material comprising: a commingled yarn that contains a continuous reinforcing fiber (A) and a continuous thermoplastic resin fiber (B) as fiber components thereof; and a thermoplastic resin fiber (C) that keeps the commingled yarn in place, a thermoplastic resin that composes the thermoplastic resin fiber (C) having a melting point 15° C. or more higher than the melting point of a thermoplastic resin that composes the continuous thermoplastic resin fiber (B).

<2> The composite material of <1>, wherein the thermoplastic resin that composes the continuous thermoplastic resin fiber (B) is a polyamide resin.

<3> The composite material of <1>, wherein the thermoplastic resin that composes the continuous thermoplastic resin fiber (B) is a polyamide resin that contains a diamine-derived structural unit and a dicarboxylic acid-derived structural unit, 50% by mole or more of the diamine-derived structural unit being derived from xylylenediamine.

<4> The composite material of any one of <1> to <3>, wherein the thermoplastic resin that composes the thermoplastic resin fiber (C) is a polyamide resin.

<5> The composite material of any one of <1> to <4>, wherein the commingled yarn is arranged in a base, and is stitched with the thermoplastic resin fiber (C) so as to be kept in place.

<6> The composite material of <5>, wherein the base is a thermoplastic resin film (D).

<7> The composite material of <6>, wherein a thermoplastic resin that composes the thermoplastic resin film (D) has a melting point 15° C. or more higher than the melting point of the thermoplastic resin that composes the continuous thermoplastic resin fiber (B).

<8> The composite material of <6> or <7>, wherein the thermoplastic resin film (D) contains a polyamide resin.

<9> The composite material of any one of <1> to <8>, wherein the continuous reinforcing fiber (A) is at least any one of carbon fiber, aramid fiber and glass fiber.

<10> The composite material of any one of <1> to <8>, wherein the continuous reinforcing fiber (A) is carbon fiber.

<11> The composite material of any one of <1> to <10>, wherein the thermoplastic resin that composes the thermoplastic resin fiber (C) has a melting point 15 to 100° C. higher than the melting point of the thermoplastic resin that composes the continuous thermoplastic resin fiber (B).

<12> The composite material of any one of <1> to <11>, wherein the continuous reinforcing fiber (A) in the commingled yarn has a dispersion of 60 to 100%.

<13> The composite material of any one of <1> to <12>, wherein a plurality of commingled yarns are arranged in parallel in one direction to form a layer; over the commingled yarn layer, a plurality of commingled yarns are arranged in parallel to form a layer, in a direction 10° to 90° away from the parallel direction of the aforementioned commingled yarn; and the thermoplastic resin fiber (C) keeps the commingled yarn layer in place.

<14> The composite material of any one of <1> to <13>, wherein the composite material is a non-crimp fabric.

<15> The composite material of any one of <1> to <14>, wherein the commingled yarn is bundled by using a treatment agent for at least either one of the continuous reinforcing fiber (A) and the continuous thermoplastic resin fiber (B).

<16> The composite material of any one of <1> to <15>, used for manufacturing a medical brace.

<17> A method for manufacturing a composite material, the method comprising stitching a base, and a commingled yarn arranged in the base, with a thermoplastic resin fiber (C); the commingled yarn containing, as its fiber components, a continuous reinforcing fiber (A) and a continuous thermoplastic resin fiber (B); and a thermoplastic resin that composes the thermoplastic resin fiber (C) having a melting point 15° C. or more higher than the melting point of a thermoplastic resin that composes the continuous thermoplastic resin fiber (B).

<18> A method for manufacturing a composite material, the method comprising forming the composite material described in any one of <1> to <16>, at a temperature lower than the melting point of a thermoplastic resin that composes the thermoplastic resin fiber (C).

This invention now makes it possible to provide a composite material with a good appearance even after heat-processed, and also a method for manufacturing a composite material, and a method for manufacturing a molded article.

BRIEF DESCRIPTION OF DRAWINGS

FIG. 1 A schematic drawing illustrating a structure of the composite material of this invention.

FIG. 2 A conceptual drawing illustrating arrangement patterns of the commingled yarn, in this invention.

FIG. 3 A conceptual drawing illustrating a state of the commingled yarn when arranged in a three-dimensional manner, in this invention.

FIG. 4 A drawing illustrating an exemplary image processing in a method for measuring dispersion.

FIG. 5 A drawing illustrating an embodiment of the composite material of this invention.

FIG. 6 A schematic drawing illustrating another exemplary embodiment of the composite material of this invention.

FIG. 7 A drawing illustrating still another exemplary embodiment of the composite material of this invention.

DESCRIPTION OF EMBODIMENTS

This invention will be detailed below. Note that all numerical ranges in this specification given using "to", placed between numerals, mean the ranges containing both numerals as the lower and upper limits. The length of fiber in this invention is weight-average fiber length unless otherwise specifically noted.

The composite material of this invention includes, as the fiber components thereof, a commingled yarn that contains a continuous reinforcing fiber (A) and a continuous thermoplastic resin fiber (B); and a thermoplastic resin fiber (C) that keeps the commingled yarn in place, wherein a thermoplastic resin (occasionally referred to as "resin c", hereinafter) that composes the thermoplastic resin fiber (C) has a melting point 15° C. or more higher than the melting point of a thermoplastic resin (occasionally referred to as "resin b", hereinafter) that composes the continuous thermoplastic resin fiber (B). With such design, a molded article having a good appearance may be obtained. Also the composite material will have a dramatically improved mechanical strength and a good formability as compared with the case where resins having nearly equal melting points are used both for the thermoplastic resin fiber (B) and the thermoplastic resin fiber (C).

This is presumably because, by setting the melting point of the thermoplastic resin (resin c) that composes the thermoplastic resin fiber (C), which keeps the commingled yarn in place, 15° C. or more higher than the melting point of the thermoplastic resin b that composes the commingled yarn, the resin b melts earlier than the resin c when the composite material of this invention is heat-processed, and impregnates properly into the continuous reinforcing fiber (A), so that the composite material of this invention may be formed while keeping a high level of dispersion of the continuous reinforcing fiber (A) in the commingled yarn, without disturbing the continuous reinforcing fiber (A), and thereby the appearance is improved. Such suppression of disorder of the commingled yarn can also dramatically improve the mechanical strength.

Prepreg is an ever-known fiber reinforced material, having therein a continuous reinforcing fiber impregnated with a thermoplastic resin. Being known as a beneficial material, the prepreg typically needed to undergo heating process twice or more, once for impregnating the thermoplastic resin into the continuous reinforcing fiber, and another once for heat process for producing a molded article. In contrast, the composite material of this invention may produce a molded article only by a single run of heat process.

There is also known a fiber reinforced material having laminated therein a fiber sheet and a resin film. Although being beneficial, the fiber reinforced material is a laminate of a fiber sheet and a resin film, in which fiber and resin do not disperse in micro scale, but are kept away from each other. For processing, it has therefore been necessary to heat the fiber reinforced material over a long time so as to impregnate the resin into the fiber sheet. Now in this invention, the commingled yarn containing the continuous reinforcing fiber (A), which intrinsically has a high level of dispersion, may be processed while keeping such high level of dispersion, and is therefore superior to the fiber reinforced material having laminated therein the fiber sheet and a resin film, in terms of formability. With such design, also the mechanical strength may be improved.

FIG. 1 is an exemplary schematic drawing of the composite material of this invention, where reference numeral or symbol 1 stands for the composite material, 2 for the commingled yarn, (C) for the thermoplastic resin fiber (C), and (D) for the thermoplastic resin film (D).

In this embodiment, the commingled yarns 2 are arranged in one direction on the thermoplastic resin film (D), and kept in place while being stitched with the thermoplastic resin fiber (C). The commingled yarn, illustrated as being arranged in one direction in FIG. 1, may be arranged in other ways. An exemplary arrangement is shown in FIG. 2. FIG. 2 is a conceptual drawing illustrating arrangement patterns of the commingled yarns in this invention, wherein the commingled yarn in FIG. 2(a) is arranged so as to be folded, and the commingled yarns in FIG. 2(b) are arranged to form a lattice. The commingled yarns are preferably arranged according to a certain regularity not specifically limited. They may also be arranged as desired, depending on applications of the molded article.

In this invention, it is also preferable, as illustrated in FIG. 3, to arrange the commingled yarns over and over again at rims, corners or the like of the molded article where force is applied in a concentrated manner.

By the way, braided cord is one of materials having been used as a material that contains the continuous reinforcing fiber and the continuous thermoplastic resin fiber. Most typical braided cord uses the continuous reinforcing fiber as a core, and the continuous thermoplastic resin fiber wound around the core. This type of braided cord, however, has a portion where the continuous reinforcing fiber lies densely. It has therefore been difficult to stitch such dense portion of the braided cord for keeping it in place. Increase in the ratio of the continuous reinforcing fiber in the braided cord, intended for increasing the strength, has made stitching further difficult. Meanwhile, a material preliminarily impregnated with the thermoplastic resin, such as UD tape, has been likely to crack when stitched.

Now in this invention, use of the commingled yarn suitably distributes the continuous reinforcing fiber, making the composite material stitchable everywhere and easy to keep the shape. Stitching will remain easy even if the ratio of content of the continuous reinforcing fiber in the commingled yarn is elevated, or if the density of the commingled yarn in the composite material is elevated. In short, the composite material of this invention may be designed with a high degree of freedom, varying the density of the commingled yarn or the density of the continuous reinforcing fiber in the commingled yarn from low to high.

Referring now back to FIG. 1, in the embodiment shown in FIG. 1, the commingled yarns 2 are arranged in a base (thermoplastic resin film (D)), and kept in place with the thermoplastic resin fiber (C). A means for keeping them in place is exemplified by stitching. With such means, the commingled yarns will be easily kept in place. It is, however, not essential to stitch the commingled yarns to the base, so long as they can be kept in place according to a desired pattern. For example, the commingled yarns arranged as illustrated in FIG. 2(b) may be kept in place without using the base, by binding only the intersections of the commingled yarns with the thermoplastic resin fiber (C), rather than stitching them onto the base. There is another exemplary embodiment in which knitted fabrics or woven fabrics manufactured by using the commingled yarns are stacked and stitched.

The base, exemplified in FIG. 1 by the thermoplastic resin film (D), may be some other base. The base will be detailed later. The thermoplastic resin film (D) may alternatively have the commingled yarns stitched on both surfaces thereof, depending on applications.

As embodiments of the composite material of this invention, exemplified are the comingled yarns layered according to a certain regularity, and a composite material having the commingled yarns layered according to a certain regularity and kept in place by using the thermoplastic resin (C). Now "layered" does not always necessarily means that the commingled yarns are arranged densely, and that the commingled yarns are arranged in one direction. For example, layers having the commingled yarns arranged according to certain regularities as illustrated in FIG. 2(a) and FIG. 2(c) may be stacked and kept in place, and also these modes are encompassed in this embodiment. In addition, also stacks containing woven fabrics or knitted fabrics are encompassed in this embodiment.

The commingled yarn layer may be provided in the base, or may be arranged without using the base. The number of layers of the commingled yarns is two or more, and preferably 3 to 20.

Another embodiment of the composite material of this invention is exemplified by a composite material typically called "non-crimp fabric". The non-crimp fabric is known as a material having no waviness (crimp) attributable to crossing of warp and weft, unlike woven fabrics having warps and wefts crossed to each other. As a result of the absence of waviness (crimp) attributable to such crossing, the non-crimp fabric can retain unidirectionality of the commingled yarn layers, and can therefore gain a high strength and a large elasticity.

The non-crimp fabric may be embodied with a single layer, or two or more layers each having a plurality of the commingled yarns arranged in parallel in one direction to form a layer, wherein there are preferably two or more commingled yarn layers. When there are two or more commingled yarn layers, the direction of arrangement of the commingled yarns in the first layer, and the direction of arrangement of the commingled yarns in the second and succeeding layers may be same, that is, may form an angle of 0° between the direction of arrangement of the commingled yarns in the first layer and the direction of arrangement of the commingled yarns in the second and succeeding layers. It is however preferable that the angle formed between the directions of parallel arrangement of the commingled yarns in the first layer, and at least one of the second and succeeding layers exceeds 0° and does not exceeds 90°. With the angle formed between the directions of parallel arrangement of the commingles yarns in the first layer, and at least one of the second and succeeding layers set so as to exceed 0°, the obtainable non-crimp fabric will have an increased strength in two or more directions. The angle is preferably 10 to 90°, and more preferably 30 to 90°. Note that the above-described angle means the smaller one of two angles formed between the direction of parallel arrangement of the commingled yarns in one layer, and the direction of parallel arrangement of the commingled yarns in other one layer. Also note that the angle in the context of this invention is not in a strictly mathematical sense, but naturally allows ordinary errors that may occur in the technical field of this invention.

As for details of the non-crimp fabric, descriptions in JP-A-2007-46197 and JP-A-2015-521661 may be referred to, the contents of which are incorporated into this specification.

As one preferred embodiment of the non-crimp fabric in this invention, exemplified is a composite material in which a plurality of commingled yarns are arranged in parallel in one direction to form a layer, and on this commingled yarn layer, a plurality of commingled yarns are again arranged in parallel in the direction larger than 0° and not larger than 90°, and more specifically 30 to 90°, away from the direction of the parallel arrangement of the above-described commingled yarns to form a layer, and the commingled yarn layers are kept in place by stitching with the thermoplastic resin fiber (C). This sort of composite material is exemplified by the one illustrated in FIG. 5. In the composite material illustrated in FIG. 5, commingled yarns 21 are aligned in parallel to form a layer, commingled yarns 22 are arranged in parallel in the direction 45° away from the direction of arrangement of the commingled yarns 21 to form a layer, commingled yarns 23 are arranged in parallel in the direction 45° away from the direction of arrangement of the commingled yarns 22, and commingled yarns 24 are arranged in parallel again in the direction 45° away from the direction of arrangement of the commingled yarns 23. These layers of the commingled yarns arranged in parallel are kept in place by stitching with the thermoplastic resin fiber (C).

The layers, although kept in place in this embodiment by forming a Z-pattern stitching around the commingled yarns 24, may be kept in place by any other methods. The conventional fabric, having warps and wefts crossed to each other and having waviness (crimp) as a consequence, has been prone to degraded strength and elasticity. In contrast, the composite material of this embodiment can achieve high strength and elasticity, since the commingled yarns keep the unidirectionality.

Although the plurality of commingled yarns illustrated in FIG. 5 are arranged in parallel on the underlying layer of the commingled yarn, at an angle of 45° to the direction of parallel arrangement, the angle may suitably be determined within the range exceeding 0° and up to 90°, preferably from 10° to 90°, and more preferably from 30° to 90°.

The commingled yarn layers may be provided in the base, or may be arranged without using the base. Two or more, and preferably 3 to 20 layers of the commingled yarn layers are preferably used.

The topmost one of the commingled yarn layers illustrated in FIG. 5 may have a base placed thereon. The commingled yarn layers, illustrated in FIG. 5 as directly stacked to each other, may be stacked while placing any other layer between the commingled yarn layers. Such other layer placed between the commingled yarn layers is not specifically limited, and may even be a commingled yarn layer.

FIG. 6 illustrates an exemplary embodiment wherein, over the surface of one commingled yarn layer, a plurality of commingled yarns are arranged in parallel, in the direction 0° away from the direction of arrangement of the underlying commingled yarns. In FIG. 6, arrows represent the directions of arrangement of the commingled yarns, and reference numerals 31 to 36 represent layers composed of the commingled yarns. Referring now to FIG. 6, the commingled yarns are arranged in parallel in the direction 0° away from the direction of parallel arrangement of the commingled yarns in layer 31, to thereby form a layer 32; the commingled yarns are arranged in parallel in the direction 90° away from the direction of parallel arrangement of the commingled yarns in layer 32, to thereby form a layer 33; the commingled yarns are arranged in parallel in the direction 0° away from the direction of parallel arrangement of the commingled yarns in layer 33, to thereby form a layer 34; the commingled yarns are arranged in parallel in the direction 90° away from the direction of parallel arrangement of the commingled yarns in layer 34, to thereby form a layer 35; and the commingled yarns are arranged in parallel in the direction 0° away from the direction of parallel arrangement of the commingled yarns in layer 35, to thereby form a layer 36. By providing two or more successive layers having the commingled yarns arranged in the same direction as described above, the strength in this direction may be enhanced.

In this embodiment, a composite material typically having a width of 5 cm or wider, and a basis weight of 200 g/m² or more may be manufactured. The upper limits of these values of the composite material may be 200 cm or below in width, and 4000 g/m² or below in basis weight.

The non-crimp fabric in this invention may be cut in a desired size before use, or may be manufactured by arranging the commingled yarns to form a layer, originally so as to make them up into a desired shape. Alternatively as illustrated in FIG. 7, a plurality of composite materials may be combined to give a desired shape as a whole. FIG. 7 illustrates four pieces of the composite material having an identical shape and bound to each other, wherein the pieces may be bound by using the thermoplastic resin fiber (C).

<Commingled Yarn>

The commingled yarn used in this invention contains, as the fiber components, the continuous reinforcing fiber (A) and the continuous thermoplastic resin fiber (B). In the commingled yarn used in this invention, typically 95% by weight or more of continuous fiber composing the commingled yarn is configured by the continuous reinforcing fiber (A) or the continuous thermoplastic resin fiber (B).

The commingled yarn used in this invention preferably has the continuous reinforcing fiber (A) dispersed therein, and bundled by using a treatment agent for at least either one of the continuous reinforcing fiber (A) and the continuous thermoplastic resin fiber (B). In the commingled yarn used in this invention, the continuous thermoplastic resin fiber (B) remains in the form of fiber, rather than being impregnated into the continuous reinforcing fiber (A). In the commingled yarn used in this invention, a part of the continuous thermoplastic resin fiber (B) component may, however, be impregnated into the continuous reinforcing fiber. More specifically, in the commingled yarn used in this invention, the impregnation ratio of the continuous thermoplastic resin fiber (B) component is preferably 12% or below, and more preferably 10% or below. The lower limit value of the impregnation ratio is preferably 0%, but not specifically limited thereto.

For the case where the commingled yarns are arranged in curved manners, rather than in a linear manner, as illustrated in FIG. 2(a) and FIG. 3, the impregnation ratio is preferably 5% or below. With such design, the commingled yarns will be less likely to break, even if arranged in curved manners.

Meanwhile, with the impregnation ratio adjusted to 1 to 12%, and further to 7 to 12%, linearity of the continuous fiber of the commingled yarn may be kept more efficiently, and this will be more likely to advantageously enhance the mechanical strength. In particular, for the case where the composite material of this invention is intended to be used as a non-crimp fabric, the commingled yarns may be arranged more exactly by adjusting the impregnation ratio to 1 to 12%.

The impregnation ratio in the context of this invention is a value given by a method described later in EXAMPLES. Note however that if the measuring instruments described in EXAMPLES are no more available or difficult to obtain, any equivalent instruments adapted to the measurement may be used. The same will also apply to all methods for measurement described below.

The ratio of the continuous reinforcing fiber (A) in the commingled yarn is preferably 10% by weight or above, more preferably 15% by weight or above, even more preferably 20% by weight or above, yet more preferably 30% by weight or above, furthermore preferably 40% by weight or above, particularly 50% by weight or above, and even may be 55% by weight or above. The upper limit of the ratio of the continuous reinforcing fiber (A) in the commingled yarn is preferably 90% by weight or below, more preferably 80% by weight or below, even more preferably 70% by weight or below, and even may be 65% by weight or below.

The ratio of the continuous thermoplastic resin fiber (B) in the commingled yarn is preferably 10% by weight or above, more preferably 20% by weight or above, even more preferably 30% by weight or above, and even may be 35% by weight or above. The upper limit of the ratio of the continuous thermoplastic resin fiber (B) is preferably 90% by weight or below, more preferably 85% by weight or below, even more preferably 80% by weight or below, yet more preferably 70% by weight or below, furthermore preferably 60% by weight or below, particularly 50% by weight or below, and even may be 45% by weight or below.

The dispersion of the continuous reinforcing fiber (A) in the commingled yarn is preferably 60 to 100%, more preferably 63 to 100%, even more preferably 68 to 100%, and particularly 70 to 100%. Within these ranges, the commingled yarn will exhibit more uniform physical property, and will yield a molded article with an improved appearance. The molded article manufactured by using this commingled yarn will also have improved mechanical properties.

The dispersion in the context of this invention is a value given by a method described later in EXAMPLES. Note however that if the measuring instruments described in EXAMPLES are no more available or difficult to obtain, any equivalent instruments may be used (The same will also apply to all methods for measurement described below).

The commingled yarn is typically manufactured by using continuous thermoplastic resin fiber bundle and continuous reinforcing fiber bundle. The total fineness of fiber used for manufacturing a single commingled yarn (sum of the individual totals of fineness of the continuous thermoplastic resin fiber and the continuous reinforcing fiber used for manufacturing a single commingled yarn) is preferably 1000 to 100000 dtex, more preferably 1500 to 50000 dtex, even more preferably 2000 to 50000 dtex, and particularly 3000 to 30000 dtex.

The ratio of the individual totals of fineness of the continuous thermoplastic resin fiber (B) and the continuous reinforcing fiber (A) used for manufacturing a single commingled yarn (total of fineness of continuous thermoplastic resin fiber (B)/total of fineness of continuous reinforcing fiber (A)) is preferably 0.1 to 10, more preferably 0.1 to 6.0, and even more preferably 0.5 to 2.0.

The total of the number of fibers used for manufacturing a single commingled yarn (sum of the total of the number of the continuous thermoplastic resin fiber (B) and the total of the number of the continuous reinforcing fiber (A)) is preferably 100 to 100000 f, more preferably 1000 to 100000 f, even more preferably 1500 to 70000 f, and yet more preferably 2000 to 20000 f. Within these ranges, the commingled yarn will have an improved commingling performance, and the obtainable composite material will have improved physical properties and texture. There will be a less region where either fiber predominates, and instead both fiber will disperse with each other more uniformly.

The ratio of the individual totals of the number of continuous thermoplastic resin fiber (B) and the number of continuous reinforcing fiber (A) used for manufacturing a single commingled yarn (total of the number of continuous thermoplastic resin fiber (B)/total of the number of continuous reinforcing fiber (A)) is preferably 0.001 to 1, more preferably 0.001 to 0.5, and even more preferably 0.05 to 0.2. Within these ranges, the commingled yarn will have an improved commingling performance, and the obtainable composite material will have improved physical properties and texture. Again within these ranges, the continuous thermoplastic resin fiber (B) and the continuous reinforcing fiber (A) will more likely be dispersed with each other uniformly, which are intrinsically desired to be uniformly dispersed in the commingled yarn.

The commingled yarn used in this invention may be twisted. Methods for twisting may be any of known methods without special limitation. The number of turns in twisting may suitably be determined depending on types of the thermoplastic resin used for the continuous thermoplastic resin fiber, the number of fibers and fineness of the thermoplastic resin fiber; types, the number of fibers and fineness of the continuous reinforcing fiber; and the ratio of the number or fibers, or the ratio of fineness of the continuous thermoplastic resin fiber and the continuous reinforcing fiber, which is typically within the range from 1 to 200 turns/m (fiber length), more specifically 1 to 100 turns/m, even more specifically 1 to 70 turns/m, and particularly 1 to 50 turns/m. With such design, the obtainable molded article will have an improved mechanical strength.

The continuous reinforcing fiber (A) and/or the continuous thermoplastic resin fiber (B) used for the commingled yarn are preferably those preliminarily treated on the surfaces with a treatment agent. With such design, it will be more easy to obtain the commingled yarn having the continuous reinforcing fiber (A) and the continuous thermoplastic resin fiber (B) dispersed therein more uniformly, and this improves the impregnation ratio of the continuous thermoplastic resin fiber (B) component into the continuous reinforcing fiber (A) after molding.

The commingled yarn may include an additional component other than the continuous reinforcing fiber (A), the continuous thermoplastic resin fiber (B), the treatment agent for the continuous reinforcing fiber (A), and the treatment agent for the continuous thermoplastic resin fiber (B), which is exemplified by short carbon fiber, carbon nanotube, fullerene, micro cellulose fiber, talc and mica. The amount of addition of these other components is preferably 5% by weight or less of the commingled yarn.

An exemplary commingled yarn of this invention is such as containing the continuous reinforcing fiber (A) and the continuous thermoplastic resin fiber (B), with a dispersion of the continuous reinforcing fiber (A) in the commingled yarn of 60 to 100%, an impregnation ratio of the continuous thermoplastic resin fiber (B) into the continuous reinforcing fiber of 12% or below, and a length of the continuous thermoplastic resin fiber (B) exceeding 30 mm.

<<Continuous Reinforcing Fiber (A)>>

The commingled yarn used in this invention contains the continuous reinforcing fiber (A). The continuous reinforcing fiber (A) in this invention is referred to as a continuous reinforcing fiber having a fiber length exceeding 6 mm, and preferably exceeding 30 mm. For improved formability, the average fiber length of the continuous reinforcing fiber used in this invention preferably, but not limitatively, falls within the range from 1 to 20,000 m, more preferably from 100 to 10,000 m, and even more preferably 1,000 to 7,000 m.

The continuous reinforcing fiber used in this invention is typically in the form of continuous reinforcing fiber bundle in which a plurality of continuous reinforcing fibers combined into a bundle.

The continuous reinforcing fiber used in this invention preferably has a total fineness per a single commingled yarn of 100 to 50000 dtex, more preferably 500 to 40000 dtex, and even more preferably 1000 to 10000 dtex. Within these ranges, the process will be more simplified, and the obtainable commingled yarn will have improved elasticity and strength.

The continuous reinforcing fiber used in this invention preferably has a total number of fibers per a single commingled yarn of 500 to 50000 f, more preferably 500 to 20000 f, even more preferably 1000 to 15000 f, and particularly 1500 to 5000 f. Within these ranges, the continuous reinforcing fiber will show an improved dispersion in the commingled yarn.

In order to satisfy predetermined levels of the total fineness and the total number of fibers in a single commingled yarn, the continuous reinforcing fiber may be manufactured by using a single continuous reinforcing fiber bundle, or by using a plurality of continuous reinforcing fiber bundles. For the manufacture in this invention, it is preferable to use 1 to 10 continuous reinforcing fiber bundles, more preferable to use 1 to 3 continuous reinforcing fiber bundles, and even more preferable to use a single continuous reinforcing fiber.

The continuous reinforcing fiber is exemplified by glass fiber; carbon fiber; plant fiber (including Kenaf, bamboo fiber, etc.); inorganic fibers such as alumina fiber, boron fiber, ceramic fiber and metal fiber (steel fiber, etc.); and organic fibers such as aramid fiber, polyoxymethylene fiber, aromatic polyamide fiber, polyparaphenylene benzobisoxazole fiber, and ultra-high molecular weight polyethylene fiber. Among them, at least one of carbon fiber, aramid fiber and glass fiber is preferable, and at least one of carbon fiber and glass fiber is more preferable. It is particularly preferable to use carbon fiber owing to its excellent features including lightness, high strength, and high elasticity. Carbon fibers of polyacrylonitrile-base ones and pitch-base ones are preferably used. Also carbon fiber derived from plant such as lignin and cellulose may also be used.

<<Treatment Agent for Continuous Reinforcing Fiber>>

The continuous reinforcing fiber used in this invention is preferably treated with a treatment agent. The treatment agent is exemplified by sizing agent and surface treatment agent. Those described in paragraphs [0093] and [0094] of JP-B1-4894982 are preferably employed, the content of which is incorporated into this specification.

In a particular case where the thermoplastic resin having a polar group is used in this invention, it is preferable to treat the continuous reinforcing fiber with a treatment agent having a functional group that can react with the polar group on the thermoplastic resin. Such functional group that can react with the polar group on the thermoplastic resin typically forms a chemical bond with the thermoplastic resin in the process of heat-molding. The treatment agent for the continuous reinforcing fiber, having a functional group that can react with the polar group of the thermoplastic resin, preferably functions to size the continuous reinforcing fiber, or helps the individual fibers physically size, before heat-processed in the commingled yarn.

More specifically, the treatment agent used in this invention is preferably at least one of epoxy resin, urethane resin, silane coupling agent, water-insoluble polyamide resin and water-soluble polyamide resin, more preferably at least one of epoxy resin, urethane resin, water-insoluble polyamide resin and water-soluble polyamide resin, and even more preferably water-soluble polyamide resin.

The epoxy resin is exemplified by glycidyl compounds such as epoxyalkane, alkane diepoxide, bisphenol A-glycidyl ether, dimer of bisphenol A-glycidyl ether, trimer of bisphenol A-glycidyl ether, oligomer of bisphenol A-glycidyl ether, polymer of bisphenol A-glycidyl ether, bisphenol F-glycidyl ether, dimer of bisphenol F-glycidyl ether, trimer of bisphenol F-glycidyl ether, oligomer of bisphenol F-glycidyl ether, polymer of bisphenol F-glycidyl ether, stearyl glycidyl ether, phenyl glycidyl ether, ethylene oxide lauryl alcohol glycidyl ether, ethylene glycol diglycidyl ether, polyethylene glycol diglycidyl ether, and propylene glycol diglycidyl ether; glycidyl ester compounds such as glycidyl benzoate, glycidyl p-toluate, glycidyl stearate, glycidyl laurate, glycidyl palmitate, glycidyl oleate, glycidyl linoleate, glycidyl linolenate, and diglycidyl phthalate; and glycidylamine compounds such as tetraglycidylaminodiphenylmethane, triglycidylaminophenol, diglycidylaniline, diglycidyltoluidine, tetraglycidyl metaxylenediamine, triglycidyl cyanurate, and triglycidyl isocyanurate.

As the urethane resin, usable are for example urethane resins obtained by allowing polyol, or polyol obtained by transesterification between oils and fats and polyhydric alcohol, to react with polyisocyanate.

The polyisocyanate is exemplified by aliphatic isocyanates such as 1,4-tetramethylene diisocyanate, 1,6-hexamethylene diisocyanate, 2,2,4-trimethylhexamethylene diisocyanate, and 2,8-diisocyanate methyl caproate; alicyclic diisocyanates such as 3-isocyanate methyl-3,5,5-trimethylcyclohexyl isocyanate, and methylcyclohexyl-2,4-diisocyanate; aromatic diisocyanates such as toluylene diisocyanate, diphenylmethane diisocyanate, 1,5-naphthene diisocyanate, diphenylmethylmethane diisocyanate, tetraalkyldiphenylmethane diisocyanate, 4,4-dibenzyl diisocyanate, and 1,3-phenylene diisocyanate; chlorinated diisocyanates; and brominated diisocyanates. These compounds may be used independently, or as a mixture of two or more species.

The polyol is exemplified by various polyols typically used for manufacturing urethane resin, including diethylene glycol, butanediol, hexanediol, neopentyl glycol, bisphenol A, cyclohexane dimethanol, trimethylolpropane, glycerin, pentaerythritol, polyethylene glycol, polypropylene glycol, polyesterpolyol, polycaprolactone, polytetramethylene ether glycol, polythioether polyol, polyacetal polyol, polybutadiene polyol, and furan dimethanol. These compound may be used independently, or as a mixture of two or more species.

The silane coupling agent is exemplified by trialkoxy or triaryloxy silane compounds such as aminopropyl triethoxysilane, phenylaminopropyl trimethoxysilane, glycidyl propyl triethoxysilane, methacryloxypropyl trimethoxysilane, and vinyl triethoxysilane; ureidosilane; sulfidosilane; vinyl silane; and imidazole silane.

Now the water-insoluble polyamide resin means that, when 1 g of such polyamide resin is added to 100 g of water at 25° C., 99% by weight or more of which remains insoluble.

When the water-insoluble polyamide resin is used, it is preferable to use a powdery water-insoluble polyamide resin after dispersing or suspending it into water or organic solvent. Into the dispersion or suspension of such powdery water-insoluble polyamide resin, the comingled fiber bundle may be dipped, and then dried, to produce the commingled yarn.

The water-insoluble polyamide resin is exemplified by polyamide 6, polyamide 66, polyamide 610, polyamide 11, polyamide 12, xylylenediamine-based polyamide resin (preferably polyxylylene adipamide and polyxylylene sebacamide), and emulsified or dispersed product of these copolymers obtained by mixing powders of them with a nonionic, cationic or anionic surfactant, or mixture of these surfactant. The water-insoluble polyamide resin is commercially available as water-insoluble nylon emulsions, typically marketed under the trade names "Sepolsion PA" from Sumitomo Seika Chemicals Co., Ltd., and "Michem Emulsion" from Michaelman Inc.

Now the water-soluble polyamide resin means that, when 1 g of such polyamide resin is added to 100 g of water at 25° C., 99% by weight more of which remains dissolved in water.

The water-soluble polyamide resin is exemplified by modified polyamides such as acrylic acid-grafted N-methoxymethylated polyamide resin, and N-methoxymethylated polyamide resin bound by amido group. The water-soluble polyamide resins are marketed under the trade names "AQ-Nylon" from Toray Industries, Inc., and "To resin" from Nagase ChemteX Corporation.

The amount of treatment agent is preferably 0.001 to 1.5% by weight of the continuous reinforcing fiber, more preferably 0.1 to 1.2% by weight, and even more preferably 0.5 to 1.1% by weight. Within these ranges, the continuous reinforcing fiber will have an improved dispersion, and the effect of this invention will be demonstrated more effectively.

<<Method for Treating Continuous Reinforcing Fiber with Treatment Agent>>

Methods for treating the continuous reinforcing fiber with a treatment agent may be any of known ones. For example, the continuous reinforcing fiber may be put in a solution having the treatment agent dissolved therein, so as to allow the treatment agent to adhere onto the surface of the continuous reinforcing fiber. The treatment agent may alternatively be blown with air onto the surface of the continuous reinforcing fiber. It is also allowable to use the continuous reinforcing fiber preliminarily treated with a surface treatment agent or a treatment agent, or to use commercially available products after once removing the surface treatment agent or the treatment agent, and then re-treating them again so as to make a desired amount of treatment agent retained on the surfaces thereof.

<<Continuous Thermoplastic Resin Fiber (B)>>

The continuous thermoplastic resin fiber (B) in this invention means a thermoplastic resin fiber having a fiber length exceeding 6 mm, and preferably exceeding 30 mm. The continuous thermoplastic resin fiber used in this invention preferably has an average fiber length within the range from 1 to 20,000 m from the viewpoint of improving the moldability, more preferably 100 to 10,000 m, and even more preferably 1,000 to 7,000 m, but not specifically limited thereto.

The continuous thermoplastic resin fiber (B) used in this invention is composed of a thermoplastic resin composition that contains thermoplastic resin b as a major ingredient. This typically means that the thermoplastic resin b accounts for 80% by weight or more, and further 90 to 100% by weight of the thermoplastic resin composition. The thermoplastic resin composition may therefore be composed of the thermoplastic resin b only, or may contain any of known additives suitably added thereto, besides the thermoplastic resin b.

The resin b may be any of those having widely been used for the composite material, which include polyolefin resins such as polyethylene and polypropylene; polyamide resin; polyester resins such as polyethylene terephthalate and polybutylene terephthalate; polycarbonate resin; polyoxymethylene resin; polyether ketone resins such as polyether ketone, polyether ether ketone, polyether ketone, and polyether ether ketone; polyethersulfone resin; polyether sulfide resin; and thermoplastic polyimide resins such as thermoplastic polyetherimide, thermoplastic polyamide-imide, fully aromatic polyimide and semiaromatic polyimide. Polyamide resin is preferable. The thermoplastic resin composition and polyamide resin employable in this invention will be described later.

The resin b preferably has a melting point of 165 to 390° C., more preferably 165 to 375° C., even more preferably 165 to 305° C., yet more preferably 175 to 295° C., and furthermore preferably 185 to 285° C., although depending on types of the resin to be used. For the resin b if desired to have a high melting point, highly heat resistant thermoplastic resins called "super engineering plastics" may be used. Examples of the super engineering plastics include AURUM (registered trademark) from Mitsui Chemicals, Inc., and Victrex (registered trademark) PEEK Series from Victrex PLC.

The continuous thermoplastic resin fiber used in this invention is usually manufactured by using a continuous thermoplastic resin fiber bundle that is the continuous thermoplastic resin fiber gathered into a bundle. Such continuous thermoplastic resin fiber bundle preferably has a total fineness of 40 to 600 dtex per fiber bundle, more preferably 50 to 500 dtex, and even more preferably 100 to 400 dtex. Within these ranges, the obtainable commingled yarn will have therein an improved dispersion of the continuous thermoplastic resin fiber. The number of fibers composing the continuous thermoplastic resin fiber bundle is preferably 1 to 200 f, more preferably 5 to 100 f, even more preferably 10 to 80 f, and particularly 20 to 50 f. Within these ranges, the obtainable commingled yarn will have therein an improved dispersion of the continuous thermoplastic resin fiber.

In this invention, in order to manufacture a single commingled yarn, it is preferable to use 1 to 100 bundles, more preferably 1 to 50 bundles, and even more preferably 3 to 25 bundles of the continuous thermoplastic resin fiber bundle. Within these ranges, the effects of this invention will more efficiently be demonstrated.

The total fineness of the continuous thermoplastic resin fiber used for manufacturing a single commingled yarn is preferably 200 to 12000 dtex, and more preferably 1000 to 6000 dtex. Within these ranges, the effects of this invention will more efficiently be demonstrated.

The total number of the continuous thermoplastic resin fiber used for manufacturing a single commingled yarn is preferably 10 to 2000 f, more preferably 20 to 1600 f, and even more preferably 200 to 350 f. Within these ranges, the commingled yarn will have an improved commingling performance, and the obtainable composite material will have improved physical properties and texture. With the number of fibers defined to 10 f or above, the opened fibers will more likely be mixed uniformly. Meanwhile, with the number of fibers defined to 2000 f or below, there will be a less region where either fiber predominates, and instead more uniform commingled yarn will be obtained.

The continuous thermoplastic resin fiber bundle used in this invention preferably has a tensile strength of 2 to 10 gf/d.

<<Thermoplastic Resin Composition>>

The continuous thermoplastic resin fiber (B) used in this invention is preferably composed of a thermoplastic resin composition that contains the thermoplastic resin b as the major ingredient as described above, and more preferably composed of a polyamide resin composition that contains a polyamide resin as the major ingredient.

The thermoplastic resin composition used in this invention may contain an elastomer component.

The elastomer component employable here may be any of known elastomers including polyolefin-based elastomer, diene-based elastomer, polystyrene-based elastomer, polyamide-based elastomer, polyester-based elastomer, polyurethane-based elastomer, fluorine-containing elastomer and silicone-based elastomer. Polyolefin-based elastomer and polystyrene-based elastomer are preferable. For these elastomers, also preferable are modified elastomers intended for adding compatibility with the polyamide resin, obtained by modification with $\alpha,\beta$-unsaturated carboxylic acid or acid anhydride thereof, acrylamide, or derivatives of these compounds, under the presence or absence of a radical initiator.

The amount of addition of the elastomer component, when added to the thermoplastic resin composition, is preferably 5 to 25% by weight of the thermoplastic resin composition.

The thermoplastic resin composition used in this invention may contain any additive so long as the purposes and effects of this invention will not be degraded, which include stabilizers such as antioxidant and heat stabilizer, hydrolysis resistance modifier, weathering stabilizer, matting agent, UV absorber, nucleating agent, plasticizer, dispersion aid, flame retardant, antistatic agent, anti-coloring agent, anti-gelling agent, colorant and mold releasing agent. For details of these additives, paragraphs [0130] to [0155] of JP-B1-4894982 may be referred to, the content of which is incorporated into this specification. The thermoplastic resin composition used in this invention preferably, but not absolutely, contains no filler. This specifically means that the content of the filler in the thermoplastic resin composition is 3% by weight or less.

As one preferred embodiment of the thermoplastic resin composition used in this invention, exemplified is an embodiment where polyamide resin accounts for 70% by weight or more (preferably 80% by weight or more) of the thermoplastic resin composition. Such polyamide resin more preferably contains a diamine-derived structural unit and a dicarboxylic acid-derived structural unit, where 50% by mole or more of the diamine-derived structural unit is derived from xylylenediamine.

<<Polyamide Resin>>

The polyamide resin used in this invention is exemplified by polyamide 4, polyamide 6, polyamide 11, polyamide 12, polyamide 46, polyamide 66, polyamide 610, polyamide 612, polyhexamethylene terephthalamide (polyamide 6T), polyhexamethylene isophthalamide (polyamide 6I), polyamide 66/6T, polyxylylene adipamide, polyxylylene sebacamide, polyxylylene dodecamide, polyamide 9T, polyamide 9MT, and polyamide 6I/6T.

Among these polyamide resins, preferable are those containing a diamine-derived structural unit and a dicarboxylic acid-derived structural unit, with 50% by mole or more of the diamine-derived structural unit being derived from xylylenediamine (occasionally referred to as "XD-based polyamide", hereinafter), from the viewpoints of formability and heat resistance.

When the polyamide resin is a mixture, the polyamide resin preferably has a ratio of content of the XD-based polyamide of 50% by weight or more, and more preferably 80% by weight or more.

In the XD-based polyamide, preferably 70% by mole or more, and more preferably 80% by mole or more of the diamine-derived structural unit is derived from metaxylylenediamine and/or paraxylylenediamine, and preferably 50% by mole or more, more preferably 70% by mole or more, and particularly 80% by mole or more of the dicarboxylic acid-derived structural unit is derived from straight-chain aliphatic $\alpha,\omega$-dicarboxylic acid having 4 to 20 carbon atoms.

Diamines other than metaxylylenediamine and paraxylylenediamine, employable as the source diamine component for the XD-based polyamide are exemplified by aliphatic diamines such as tetramethylenediamine, pentamethylenediamine, 2-methylpentanediamine, hexamethylenediamine, heptamethylenediamine, octamethylenediamine, nonamethylenediamine, decamethylenediamine, dodecamethylenediamine, 2,2,4-trimethyl-hexamethylenediamine, and 2,4,4-trimethylhexamethylenediamine; alicyclic diamines such as 1,3-bis(aminomethyl)cyclohexane, 1,4-bis(aminomethyl)cyclohexane, 1,3-diaminocyclohexane, 1,4-diaminocyclohexane, bis(4-aminocyclohexyl)methane, 2,2-bis(4-aminocyclohexyl)propane, bis(aminomethyl)decalin, and bis(aminomethyl)tricyclodecane; and aromatic diamines such as bis(4-aminophenyl) ether, paraphenylene diamine, and bis(aminomethyl)naphthalene. These compounds may be used independently, or as a mixture of two or more species.

When diamines other than xylylenediamine are used as the diamine component, the ratio of content thereof is less than 50% by mole of the diamine-derived structural unit, preferably 30% by mole or less, more preferably 1 to 25% by mole, and particularly 5 to 20% by mole.

The straight-chain aliphatic $\alpha,\omega$-dicarboxylic acid having 4 to 20 carbon atoms, suitably used as the source dicarboxylic acid component for the polyamide resin, is exemplified by aliphatic dicarboxylic acids such as succinic acid, glutaric acid, pimelic acid, suberic acid, azelaic acid, adipic acid, sebacic acid, undecanedioic acid, and dodecanedioic acid. These compounds may be used independently, or as a mixture of two or more species. Among them, adipic acid or sebacic acid is preferable from the viewpoint of optimizing the melting point of the polyamide resin to be molded. Sebacic acid is particularly preferable.

Dicarboxylic acid component, other than the straight-chain aliphatic $\alpha,\omega$-dicarboxylic acid having 4 to 20 carbon atoms, is exemplified by phthalic acid compounds such as isophthalic acid, terephthalic acid, orthophthalic acid; and naphthalene dicarboxylic acids including isomers such as 1,2-naphthalenedicarboxylic acid, 1,3-naphthalenedicarboxylic acid, 1,4-naphthalenedicarboxylic acid, 1,5-naphthalenedicarboxylic acid, 1,6-naphthalenedicarboxylic acid, 1,7-naphthalenedicarboxylic acid, 1,8-naphthalenedicarboxylic acid, 2,3-naphthalenedicarboxylic acid, 2,6-naphthalenedicarboxylic acid, and 2,7-naphthalenedicarboxylic acid. These compounds may be used independently, or as a mixture of two or more species.

When dicarboxylic acids other than the straight-chain aliphatic $\alpha,\omega$-dicarboxylic acid having 4 to 20 carbon atoms are used as the dicarboxylic acid component, it is preferable to use terephthalic acid or isophthalic acid, from the viewpoints of moldability and barrier performance. Ratio of terephthalic acid or isophthalic acid is preferably 30% by mole or less of the dicarboxylic acid structural unit, more preferably 1 to 30% by mole, and particularly 5 to 20% by mole.

Besides the diamine component and the dicarboxylic acid component, any copolymerizable component may be used as a component composing the polyamide resin, so long as the effects of this invention will not be degraded, wherein the component including lactams such as $\varepsilon$-caprolactam and laurolactam; aminocaproic acid; and aliphatic aminocarboxylic acids such as aminocaproic acid and aminoundecanoic acid.

The polyamide resin used in this invention preferably has a number-average molecular weight (Mn) or 6,000 to 30,000, more preferably 8,000 to 28,000, even more preferably 9,000 to 26,000, yet more preferably 10,000 to 24,000, and particularly 11,000 to 22,000. Within these ranges, the heat resistance, elasticity, dimensional stability and moldability will be improved.

The number-average molecular weight (Mn) in this context is calculated from the equation below, using terminal amino group concentration [NH$_2$] (microequivalents/g) and terminal carboxy group concentration [COOH] (microequivalents/g) of the polyamide resin:

Number-average molecular weight (Mn)=2,000,000/
([COOH]+[NH$_2$]).

The polyamide resin used in this invention preferably has a dispersity (weight-average molecular weight/number-average molecular weight (Mw/Mn)) of 1.8 to 3.1. The dispersity is more preferably 1.9 to 3.0, and even more preferably 2.0 to 2.9. With the dispersity fallen within these ranges, the composite material with excellent mechanical properties will more likely be obtained.

The dispersity of polyamide resin is controllable by suitably selecting types and amounts of initiator or catalyst used for polymerization, or polymerization conditions including reaction temperature, pressure and time. Alternatively, the dispersity is also controllable by mixing two or more types of polyamide resins obtained under different polymerization conditions, or by subjecting the polymerized polyamide resin to fractional precipitation.

The dispersity may be determined by GPC, and may more specifically be given as standard polymethyl methacrylate (PMMA) equivalent values, through measurement by using a measuring instrument "HLC-8320GPC" from Tosoh Corporation, two sets of "TSK gel Super HM-H" columns from Tosoh Corporation, a 10 mmol/l sodium trifluoroacetate in hexafluoroisopropanol (HFIP) as an eluant, conducted under conditions including a resin concentration of 0.02% by weight, a column temperature of 40° C., and a flow rate of 0.3 ml/min, with use of a refractive index detector (RI). An analytical curve is prepared by dissolving PMMA in HFIP, at six levels of concentration.

The polyamide resin, when moistened with water, preferably has a flexural modulus retention of 85% or larger. With the flexural modulus retention under moistened condition adjusted to this level, the molded article will be less likely to degrade the physical properties under hot and humid conditions, and will be less likely to cause warping or other deformation.

The flexural modulus retention of the polyamide resin, when moistened with water, is defined by the ratio (%) of flexural modulus of a bend test specimen of polyamide resin, molded in compliance with JIS K7171, measured at a moisture content of 0.5% by weight, relative to flexural modulus measured at a moisture content of 0.1% by weight. A large value of the ratio means that the flexural modulus is less likely to decrease even under moisture. Now, the flexural modulus is a value obtained by measurement according to JIS K7171.

The flexural modulus retention under moisture is more preferably 90% is larger, and even more preferably 95% or larger.

The flexural modulus retention of polyamide resin when moistened is controllable, typically based on the ratio of mixing of paraxylylenediamine and metaxylylenediamine, wherein the larger the ratio of paraxylylenediamine will be, the better the flexural modulus retention will be. It is also adjustable by controlling the crystallinity of the bend test specimen.

Water absorption of the polyamide resin is determined by immersing the bend test specimen, molded according to JIS K7171, into water at 23° C. for one week, taking it out, wiping the water away, and then subjecting the specimen to measurement immediately thereafter. The water absorption is preferably 1% by weight or below, more preferably 0.6% by weight or below, and even more preferably 0.4% by weight or below. Within these ranges, the molded article will easily be prevented from being deformed due to absorption of water, the composite material will be suppressed from foaming during molding typically under pressure and heating, and thereby the obtainable molded article will contain less bubbles.

The polyamide resin is suitably used when it has the terminal amino group concentration ([$NH_2$]) preferably less than 100 microequivalents/g, more preferably 5 to 75 microequivalents/g, and even more preferably 10 to 60 microequivalents/g; and the terminal carboxy group concentration ([COOH]) preferably less than 150 microequivalents/g, more preferably 10 to 120 microequivalents/g, and even more preferably 10 to 100 microequivalents/g. By using the polyamide resin with the terminal group concentrations of these levels, the polyamide resin will have the viscosity stabilized easily when it is processed into film or fiber, and will more likely be reactive with a carbodiimide compound described later.

The polyamide resin is preferable if it has a ratio of the terminal amino group concentration relative to the terminal carboxy group concentration ([$NH_2$]/[COOH]) of 0.7 or smaller, which is more preferably 0.6 or smaller, and particularly 0.5 or smaller. The polyamide resin having the ratio larger than 0.7 will occasionally make it difficult to control the molecular weight during polymerization.

The terminal amino group concentration may be measured by dissolving 0.5 g of polyamide resin into 30 ml of phenol/methanol (4:1) mixed solvent under stirring at 20 to 30° C., and titrating the solution with a 0.01 N hydrochloric acid. The terminal carboxy group concentration may be determined by dissolving 0.1 g of polyamide resin into 30 ml of benzyl alcohol at 200° C., adding thereto 0.1 ml of phenol red solution at 160° C. to 165° C., titrating the solution with a titrant obtained by dissolving 0.132 g of KOH into 200 ml of benzyl alcohol (0.01 mol KOH/l). The end point of titration may be judged by a point where the color changes from yellow to red, and kept unchanged.

As for a method for manufacturing the polyamide resin, the description in paragraphs [0052] to [0053] of JP-A-2014-173196 may be referred to, the content of which is incorporated into this specification.

In this invention, the melting point of the polyamide resin is preferably 150 to 310° C., more preferably 180 to 300° C., and even more preferably 180 to 250° C.

The glass transition point of the polyamide resin is preferably 50 to 100° C., more preferably 55 to 100° C., and particularly 60 to 100° C. Within these ranges, the heat resistance will likely be improved.

The melting point in the context of this invention is defined by a temperature at the endothermic peak top in DSC (differential scanning calorimetry) during a heating process, and is more specifically a value obtained by measurement according to the method described later in EXAMPLES.

The glass transition temperature is measured after once heating and melting a sample so as to cancel any influences of the thermal history on the crystallinity, and by heating the sample again. The measurement may be conducted typically by using "DSC-60" from Shimadzu Corporation, approximately 1 mg of the sample, and nitrogen as an atmospheric gas fed at a flow rate of 30 ml/min, wherein the polyamide resin is melted under heating at a heating rate of 10° C./min from room temperature up to a temperature not lower than a predicted melting point, and the melting point was determined by a temperature at which the endothermic peak becomes deepest. The molten polyamide resin was then rapidly cooled on dry ice, and re-heated up to a temperature not lower than the melting point at a heating rate of 10° C./min, to determine the glass transition point.

For low crystallinity resin that is less likely to form a crystal structure, the melting point may be measured after pre-treating the resin so as to make the melting point well recognizable. The pre-treatment is exemplified by heating.

<<Treatment Agent for Continuous Thermoplastic Resin Fiber>>

It is also preferable to treat the surface of the continuous thermoplastic resin fiber (B) used in this invention, with a treatment agent. This embodiment can improve dispersion of the continuous reinforcing fiber (A) in the commingled yarn. Types of the treatment agent are not specifically limited, so far as they functions to size the continuous thermoplastic resin fiber (B). The treatment agent is exemplified by ester-based compound, alkylene glycol-based compound, polyolefin-based compound and phenyl ether-based compound. More specifically, surfactants are preferable.

The amount of the treatment agent for the continuous thermoplastic resin fiber is preferably 0.1 to 2% by weight of the continuous thermoplastic resin fiber, and more preferably 0.5 to 1.5% by weight. Within these ranges, the continuous thermoplastic resin fiber will disperse more uniformly, and more uniform commingled yarn will likely be obtained. In the process of manufacturing the commingled yarn, the continuous thermoplastic resin fiber may occasionally be broken, due to frictional force applied by a machine or frictional force that effects among the fibers. Within the above-described ranges, the fibers may more effectively be prevented from being broken. In addition, the continuous thermoplastic resin fiber may effectively be prevented from being broken under mechanical stress that is applied to obtain a uniform commingled yarn.

<<<Method for Treating Continuous Thermoplastic Resin Fiber (B) with Treatment Agent>>

Methods for treating the continuous thermoplastic resin fiber (B) with a treatment agent are not specifically limited so long as they can achieve intended objectives. For example, a solution having the treatment agent dissolved therein is applied to the continuous thermoplastic resin fiber (B), so as to allow the treatment agent to adhere onto the surface of the continuous thermoplastic resin fiber (B). The treatment agent may alternatively be blown with air onto the surface of the continuous thermoplastic resin fiber.

<Thermoplastic Resin Fiber (C)>

The thermoplastic resin fiber (C) used in this invention is composed of a thermoplastic resin composition that contains thermoplastic resin c as a major ingredient. In the thermoplastic resin composition, which is a source of the thermoplastic resin fiber (C), the thermoplastic resin c typically accounts for 50% by weight or more, more preferably 60% by weight or more, and may even account for 70% by weight or more.

For the resin c, a wide variety of materials used for the composite material may be employed, including polyolefin resins such as polyethylene and polypropylene; polyamide resin; polyester resins such as polyethylene terephthalate and polybutylene terephthalate; polycarbonate resin; polyoxymethylene resin; polyether ketone resins such as polyether ketone, polyether ether ketone, polyether ketone ketone and polyether ether ketone ketone; polyethersulfone resin; polyether sulfide resin; and thermoplastic polyimide resins such as thermoplastic polyetherimide, thermoplastic polyamide-imide, fully aromatic polyimide and semiaromatic polyimide. In this invention, the resin c is preferably polyamide resin. The polyamide resins that may preferably be employed are specifically exemplified by the polyamide resins described above in the section titled "Continuous Thermoplastic Resin Fiber (B)". The thermoplastic resin composition as a source for the thermoplastic resin fiber (C) may contain any components other than the thermoplastic resin, which are synonymous to those described under the title of Continuous Thermoplastic Resin Fiber (B), with the same preferred ranges.

Although depending on types of resin in use, the resin c preferably has a melting point of 180 to 405° C., more preferably 180 to 390° C., even more preferably 180 to 320° C., yet more preferably 190 to 310° C., and furthermore preferably 200 to 300° C. The length of the thermoplastic resin fiber (C) used in this invention is not specifically limited so long as they can keep the commingled yarn in place. From the viewpoint of easiness of processing, the thermoplastic resin fiber preferably has a length of 6 mm or longer, and more preferably 20 mm or longer. In this invention, the commingled yarn may be kept in place with only a single thermoplastic resin fiber (C), or the commingled yarn may be kept in place at separate portions with two or more thermoplastic resin fibers (C), or still alternatively the commingled yarn may be kept in place with two or more bundled thermoplastic resin fibers (C).

The thermoplastic resin fiber (C) typically has a fineness of 10 to 200 dtex, preferably 50 to 150 dtex, and more preferably 100 to 150 dtex. The thermoplastic resin fiber (C) may be used in its original form, or in the form of multi-ply fiber such as two-ply and three-ply fibers.

<Relation Between Melting Points of Resin b and Resin c>

In this invention, the melting point of the thermoplastic resin c that composes the thermoplastic resin fiber (C) is 15° C. or more higher than the melting point of the thermoplastic resin b that composes the continuous thermoplastic resin fiber (B). With such design, the resin b is allowed to impregnate without disturbing the state of dispersion of the continuous reinforcing fiber (A), and thereby the obtainable molded article will have an improved appearance.

Now for the case where the resin b is composed of two or more species of resin, the melting point of the resin b is represented by the melting point of the resin whose melting point is higher. If the resin b has two or more melting points, the melting point of the resin b is represented by the higher one. Meanwhile, for the case where the resin c is composed of two or more species of resin, the melting point of the resin c is represented by the melting point of the resin whose content is larger. If the resin c is composed of nearly equal amounts of two or more species of resin, the melting point of the resin c is represented by the melting point of the resin whose melting point is highest.

For the case where the resin c has two or more melting points, the melting point of the resin c is represented by the higher one.

The difference between the melting point of the resin c and the melting point of the resin b (melting point of resin c −melting point of resin b) may be 16° C. or larger, even may be 17° C. or larger, and particularly may be 18° C. or larger. Although not specifically limited, the upper limit of the difference between the melting point of the resin c and the melting point of the resin b is preferably 100° C. or smaller, more preferably 80° C. or smaller, and particularly 75° C. or smaller. Within these ranges, also the resin c can melt during molding under heating, after the resin b melted, making the thermoplastic resin fiber (C) less recognizable, and thereby the molded article will have an improved appearance.

This invention also discloses an embodiment using, as the resin c that composes the thermoplastic resin fiber (C), resin c1 having a melting point 15° C. or more higher than that of the resin b, and resin c2 having a melting point lower than that of the resin b. In this embodiment, the commingled yarn that contains the resin b is kept in place with the thermoplastic resin fiber (C) that contains the resin c1 and the resin c2, and the article is then preliminarily heated at a temperature not higher than the melting point of the resin b, during which only the resin c2 melts to tentatively bind the entire portion, and can improve the operability.

In the process of keeping the commingled yarn in place, the thermoplastic resin fiber (C) stitched so as to embroider the base can give a pattern with good design. Therefore the resin c may also be remained intact, without being melted. The resin c in this case preferably has a melting point 20 to 100° C. higher, and more preferably 30 to 100° C. higher than the melting point of the resin b.

<Base>

In this invention, the commingled yarns are preferably arranged in the base, and kept in place by stitching with the thermoplastic resin fiber (C). The base is exemplified by resin film, reinforcing fiber-containing mat material, woven fabric or knitted fabric of glass fiber or other fibers, and metal foil. A preferred embodiment of this invention is exemplified by a case where the thermoplastic resin film (D) is used. The base typically, but not specifically, has a thickness of 20 to 100 μm.

The reinforcing fiber-containing mat material is beneficially used, since a mat component may be fed into ribs or the like in the process of press molding, enabling integrated molding.

Stitching may be provided by any known methods for stitching and embroidering. It suffices that the base and the commingled yarn are kept in place so as not to be largely deformed during carrying or transportation.

<<Thermoplastic Resin Film (D)>>

The thermoplastic resin film (D) used in this invention is a thermoplastic resin-containing film, in which a thermoplastic resin (may occasionally be referred to as "resin d", hereinafter) typically accounts for 30 to 100% by weight of the film. The thermoplastic resin is exemplified by polyolefin resins such as polyethylene and polypropylene; polyester resins such as polyamide resin, polyethylene terephthalate and polybutylene terephthalate; polycarbonate resin; polyoxymethylene resin; polyether ketone resins such as polyether ketone, polyether ether ketone, polyether ketone ketone, and polyether ether ketone ketone; polyether sulfone resin; polyether sulfide resin; and thermoplastic polyimide resins such as thermoplastic polyetherimide, thermoplastic polyamide-imide, fully aromatic polyimide and semiaromatic polyimide. Polyamide resin is preferable. The polyamide resin employable in this invention is exemplified by the polyamide resins described above regarding in relation to "resin b". Polyamide 6 and polyamide 66 are preferable.

The thermoplastic resin film (D) used in this invention may contain any components other than the thermoplastic resin. Such components are synonymous to those described under the title of Continuous Thermoplastic Resin Fiber (B), with the same preferred ranges.

The resin d preferably has a melting point of 180 to 405° C., more preferably 180 to 390° C., even more preferably 180 to 320° C., yet more preferably 190 to 310° C., and furthermore preferably 200 to 300° C. If the resin d is composed of two or more species of resin, the melting point of the resin d is represented by the melting point of the resin whose melting point is higher. If the resin d has two or more melting points, the melting point of the resin d is represented by the higher one.

In this invention, resin d preferably has a melting point 15° C. or more higher than the melting point of the resin b, which is more preferably 20 to 80° C. higher, and even more preferably 25 to 76° C. higher. With such design, the resin b is allowed to melt earlier than the resin d, in the process of molding under heating.

<Combination of Resin b, Resin c and Resin d>

The resin b, resin c and resin d in the composite material of this invention are preferably combined so as to satisfy the above-described relation of melting points. It is particularly preferable that the resin b is mainly composed of an XD-based polyamide, and the resin c and the resin d are mainly composed of polyamide 66 and XD-based polyamide, respectively.

In this invention, it is also preferable that a high-melting-point resin is used for both of the resin b and the resin c, in view of obtaining a highly heat resistant composite material. One preferred embodiment relates to use of at least one of polyether ketone resin and polyimide resin, and one more preferred embodiment relates to use of at least polyether ketone resin. More specifically, exemplified are an embodiment using a polyether ether ketone resin (typically with m.p. 343° C.) for the resin b, and a polyimide resin (for example, AURUM from Mitsui Chemicals, Inc., m.p. 388° C.) for the resin c; and an embodiment using polyether ketone ketone resins having different melting points (for example, KEPSTAN 7002 (m.p. 331° C.) and KEPSTAN 8002 (m.p. 357° C.) from ARKEMA) for the resin b and the resin c, respectively.

<Method for Manufacturing Composite Material>

The method for manufacturing a composite material of this invention may be any known methods without special limitation.

For example, the method includes stitching a base, and a commingled yarn arranged in the base with a thermoplastic resin fiber (C); the commingled yarn containing, as its fiber components, a continuous reinforcing fiber (A) and a continuous thermoplastic resin fiber (B); and a thermoplastic resin that composes the thermoplastic resin fiber (C) having a melting point 15° C. or more higher than the melting point of a thermoplastic resin that composes the continuous thermoplastic resin fiber (B).

<Method for Manufacturing Molded Article>

According to the method for manufacturing a molded article, the composite material of this invention is preferably molded at a temperature lower than the melting point of the thermoplastic resin that composes the thermoplastic resin fiber (C), but not limited thereto. Under such molding conditions, the resin c will be less likely to melt, instead allowing the resin b to melt first. As a consequence, the resin b, or a thermoplastic resin composition that contains resin b is suitably allowed to be impregnated into the continuous reinforcing fiber (A), while keeping the state of dispersion of the continuous reinforcing fiber (A) and the continuous thermoplastic resin fiber (B). After the resin b melts, the resin c may be allowed to melt, or remained unmelted. The resin c is, however, preferably melted since the resin c will be less recognizable in the molded article.

The molding temperature is preferably 5 to 50° C. lower than the melting point of the resin c, more preferably 10 to 34° C. lower, even more preferably 10 to 30° C. lower, yet more preferably 10 to 28° C. lower, and furthermore preferably 10 to 25° C. lower. The heating time may typically, but not limitatively, be 1 to 10 minutes. Pressure may optionally be applied, in the range from 1 to 5 MPa or around.

The molding temperature preferably falls within the range from 180 to 300° C., and more preferably from 190 to 270° C., although depending on types of the resin in use.

The molding may be followed by post-heating based on temperature elevation. Such post-heating will make the thermoplastic resin fiber (C) further less recognizable. The heating temperature in this process is preferably (melting point of resin c−20° C.) or above, and more preferably (melting point of resin c−15° C.) or above. The upper limit of post-heating temperature is preferably not lower than the melting point of resin c, and more preferably not lower than (melting point of resin c−5° C.). The heating time in this process is typically 30 to 300 seconds.

For the case where the molding is followed by the post-heating based on temperature elevation, a relatively low molding temperature (for example, approximately 20 to 55° C. lower, and more specifically 25 to 50° C. lower, than the melting point of the resin c) will be good enough to make the resin c less recognizable.

An embodiment in which the molding is not followed by temperature elevation is preferred over an embodiment in which the molding is followed by post-heating based on temperature elevation, from the viewpoints of shorter process time and operability. The embodiment in which the molding is followed by temperature elevation can, however, allow impregnation of the thermoplastic resin and reaction with the continuous reinforcing fiber at the interface to proceed more effectively, and can produce the molded article with an improved mechanical strength.

In this invention, the molded article may be covered with a thermosetting resin.

<Applications of Molded Article>

The molded article obtained by molding the composite material of this invention is versatile in various fields including automobile parts, aircraft and other transport aircraft parts, general machinery parts, precision equipment parts, electronic/electric equipment parts, office automation equipment parts, building material/housing equipment parts, medical device, leisure time/sport goods, playing tools, medical supplies, daily goods including food wrapping film, and defense/aerospace products, without special limitation. This is particularly suitable for materials for molding medical brace (knee ankle foot orthosis, etc.); window frames of automobile, train and ship; frame of goggles portion of helmet; spectacle frame; and safety shoes. The composite material of this invention is particularly beneficial as molding materials for medical brace and secondary structural member of automobile.

EXAMPLES

This invention will further be detailed below, referring to Examples. All materials, amounts of consumption, ratios, process details and procedures described in Examples below may suitably be modified, without departing from the spirit of this invention. Therefore, the scope of this invention will never be limited by the specific Examples below.

The following materials were used.
1. Thermoplastic Resin b

Synthesis Example 1: MPXD10

Into a reaction vessel equipped with a stirrer, a partial condenser, a total condenser, a thermometer, a dropping funnel, a nitrogen feeding pipe, and a strand die, placed were 10 kg (49.4 mol) of sebacic acid (TA grade, from Itoh Oil Chemicals Co., Ltd.) and 11.66 g of sodium acetate/sodium hypophosphite monohydrate (molar ratio=1/1.5), the atmosphere was thoroughly replaced with nitrogen gas, and the content was allowed to melt under heating up to 170° C., while stirring under a low flow rate of nitrogen gas.

To the molten sebacic acid kept under stirring, 6.647 kg of mixed xylylenediamine containing metaxylylenediamine (from Mitsubishi Gas Chemical Company) and paraxylylenediamine (from Mitsubishi Gas Chemical Company), whose molar ratio is 70/30 (metaxylylenediamine=34.16 mol, paraxylylenediamine=14.64 mol), was added dropwise, and the inner temperature was continuously elevated over 2.5 hours up to 240° C., while removing the condensed water out of the system.

After completion of the dropwise addition, the inner temperature was elevated, the inner pressure of the vessel was reduced when the inner temperature reached 250° C., the inner temperature was further elevated, and kept at 255° C. for 20 minutes so as to allow the melt polycondensation to proceed. The system was then pressurized with nitrogen gas, the resultant polymer was drawn out through the strand die, and then pelletized, to obtain polyamide resin MPXD10.

The thus obtained polyamide resin was found to have a melting point of 213° C., and a number-average molecular weight of 15,400.

Synthesis Example 2: MXD10

Polyamide resin MXD10 was obtained in the same way as in Synthesis Example 1, except that the mixed xylylenediamine containing metaxylylenediamine and paraxylylenediamine was replaced with an equal amount of metaxylylenediamine.

The thus obtained polyamide resin was found to have a melting point of 190° C., and a number-average molecular weight of 14,900.

MXD6: Metaxylylene adipamide resin (Grade 56001, from Mitsubishi Gas Chemical Company), melting point=237° C., number-average molecular weight=16,800

2. Continuous Reinforcing Fiber (A)

Continuous carbon fiber: Pyrofil-TR-505-12000-AD from Mitsubishi Rayon Co., Ltd., 8000 dtex, number of fibers=12,000 f. Coated with an epoxy resin.

Continuous glass fiber: from Nitto Boseki Co., Ltd., 1350 dtex, the number of fibers=800 f.

Continuous aramid fiber: Purchased from FRP-ZONE.COM.

3. Thermoplastic Resin Film (D)

Polyamide 66 pellets were fed to a single screw extruder (PTM-30, from PLABOR Research Laboratory of Plastics Technology Co., Ltd) with a T-die, having a cylinder diameter of 30 mm. The resin was melt-kneaded at a cylinder temperature of 215° C. to 290° C., and a number of rotation of screw of 30 rpm. After the melt-kneading, the resin was extruded through the T-die into film, solidified on a cooling roll, to obtain a 100 μm thick film.

4. Thermoplastic Resin c

MXD6: Same as MXD6 used for the thermoplastic resin b.
MPXD10: Same as MPXD10 used for the thermoplastic resin b.
PA66: CM3001N, from Toray Industries, Inc.

Synthesis Example 3: MPXD6

Polyamide resin MPXD6 was obtained in the same way as in Synthesis Example 1, except that the sebacic acid was replaced with an equimolar of adipic acid (from Rhodia S.A.), and that, after completion of the dropwise addition, the inner pressure of the reaction vessel was reduced when the inner temperature reached 275° C., and the inner temperature was further elevated up to 280° C.

The thus obtained polyamide resin was found to have a melting point of 255° C., and a number-average molecular weight of 17,800.

Synthesis Example 4: PXD10

Polyamide resin PXD10 was obtained in the same way as in Synthesis Example 1, except that the mixed xylylenediamine containing metaxylylenediamine and paraxylylenediamine was replaced with an equimolar of paraxylylenediamine, and that, after completion of the dropwise addition, the inner pressure of the reaction vessel was reduced when the inner temperature reached 290° C., and the inner temperature was further elevated up to 295° C.

The thus obtained polyamide resin was found to have a melting point of 290° C., and a number-average molecular weight of 17,000.

5. Measurement Methods
(Melting Point)

Using DSC-60 from Shimadzu Corporation, and nitrogen gas as an atmospheric gas fed at a flow rate of 30 ml/min, approximately 1 mg of sample was allowed to melt by heating at a heating rate of 10° C./min, from room temperature (25° C.) up to a temperature not lower than a predicted melting point, the molten polyamide resin was then rapidly cooled on dry ice, and re-heated up to a temperature not lower than the melting point at a heating rate of 10° C./min, during which an endothermic peak was observed to determine the melting point that is given by a temperature at which the peak falls deepest.

(Fineness)

The weight per 1 m of the commingled yarn or the thermoplastic resin fiber was measured, and converted to fineness.

Example 1

(Manufacture of Continuous Thermoplastic Resin Fiber (B))

A thermoplastic resin listed in Table below was processed into fibers according to the procedures below.

The thermoplastic resin was melted in a single screw extruder with a 30 mm diameter screw, and extruded through a 60-hole die into strands, stretched while being taken up on a roll, to obtain a wound article of thermoplastic resin fiber bundle. The melting temperature was 15° C. higher than the melting point of the resin.

(Manufacture of Thermoplastic Resin Fiber (C))

The thermoplastic resin listed in Table below was processed into fibers according to the procedures below.

The thermoplastic resin was melted in a single screw extruder with a 30 mm diameter screw, and extruded through a 34-hole die into strands, stretched while being taken up on a roll, to obtain a wound article of thermoplastic resin fiber bundle. The melting temperature was 15° C. higher than the melting point of the resin.

(Manufacture of Commingled Yarn)

The commingled yarn was manufactured according to the procedures below.

The continuous thermoplastic resin fiber and the continuous reinforcing fiber were respectively drawn out from the wound articles, and blown with air for opening while they are allowed to pass through a plurality of guides. While opened, the continuous thermoplastic resin fiber and the continuous reinforcing fiber were gathered into one bundle, and further blown with air while they are allowed to pass through a plurality of guides to improve uniformity. The commingled yarn was thus obtained.

(Measurement of Dispersion)

The dispersion of the commingled yarn was observed and measured as described below.

The commingled yarn was cut, embedded into an epoxy resin, the embedded commingled yarn was polished on its cross section taken perpendicular to the longitudinal direction, and the cross section was photographed under a ultra-depth 3D profiling color microscope VK-9500 (controller unit)/VK-9510 (measurement unit) (from Keyence Corporation). As illustrated in FIG. 4, six additional lines were radially drawn on the obtained image at regular angular intervals, and the length of regions of the reinforcing fiber, fallen on each of the additional lines, were measured and denoted as a1, a2, a3 . . . ai (i=n). Also the length of regions of the thermoplastic resin fiber, fallen on each of the additional lines, were measured and denoted as b1, b2, b3 . . . bi (i=m). The dispersion was calculated by the equation below.

[Mathematical Formula 1]

$$\left[1 - \left(\frac{1}{n \text{ or } m} \times \frac{\sum_{i=1}^{n \text{ or } m}(a_i \text{ or } b_i)}{\sum_{i=1}^{n \text{ or } m}(a_i) + \sum_{i=1}^{n \text{ or } m}(b_i)}\right)\right] \times 100 \ (\%)$$

(Measurement of Impregnation Ratio)

The commingled yarn was cut, embedded into an epoxy resin, the embedded commingled yarn was polished on its cross section taken perpendicular to the longitudinal direction, and the cross section was photographed under a ultra-depth 3D profiling color microscope VK-9500 (controller unit)/VK-9510 (measurement unit) (from Keyence Corporation). On the thus obtained cross-sectional image, regions of the continuous reinforcing fiber having the molten thermoplastic resin fiber component impregnated therein were selected using image analysis software ImageJ, and the areas were measured. The impregnation ratio was given by percentage of the areas of the regions where the thermoplastic resin component was impregnated into the continuous reinforcing fiber, relative to the photographed cross-sectional area.

(Manufacture of Composite Material)

On the polyamide 66 film (thermoplastic resin film (D)), the commingled yarns obtained above were arranged as illustrated in FIG. 2(a), and fixed by stitching to the polyamide 66 film, using a thermoplastic resin fiber (C) listed in Table below, given in the form of two-ply fiber. A composite material was thus obtained.

(Molding of Composite Material)

The thus obtained fiber reinforced composite material was molded by pressing at a molding temperature listed in Table below, at a pressure of 2 MPa for 5 minutes.

(Appearance 1: Disorder of Continuous Reinforcing Fiber)

The appearance of the obtained molded article was evaluated according to the criteria below:

◯: almost no disorder in continuous reinforcing fiber (A); and x: recognizable disorder in continuous reinforcing fiber (A) (not "◯" as above)

(Appearance 2: Stitching with Thermoplastic Resin Fiber (C))

The obtained molded article was evaluated according to the criteria below:

A: thermoplastic resin fiber (C) remains unmelted and much recognizable; and

B: thermoplastic resin fiber (C) melted and less recognizable.

(Ratio of Improvement in Mechanical Strength)

Tensile strength of the obtained molded article (referred to as "molded article 1") was measured according to the methods described in ISO 527-1 and ISO 527-2, at a measurement temperature of 23° C., an inter-chuck distance of 50 mm, and tensile speed of 50 mm/min.

The tensile strength was measured also for a molded article (referred to as "molded article 2") obtained in the same way as in Example 1, except that the thermoplastic resin fiber (C) was replaced with the thermoplastic resin fiber (B) used in Example 1. The ratio of improvement was determined by assessing molded article 1 relative to molded article 2.

Ratio of improvement=(Tensile strength of molded article 1)/(Tensile strength of molded article 2)

(Moldability)

The obtained molded article was subjected to the measurement below to evaluate the moldability. The composite material before heat-molded was marked at two arbitrary points 5 cm away from each other, and the distance between these two points was measured again after heat molding, to find the change ratio.

◯: size of molded article<size measured when kept in place±2%;

x: size of molded article≥size when measured kept in place±2%.

Examples 2 to 13, Comparative Example 1

The procedures were conducted in the same way as in Example 1, except that the type of the continuous reinforcing fiber (A), type of the continuous thermoplastic resin fiber (B), type of the thermoplastic resin fiber (C), and molding temperature of the composite material were changed as summarized in Tables below. In Example 10 and Example 11, the molding was further followed by heating at the temperatures listed in Table for 180 seconds. The ratio of improvement in the mechanical strength was determined based on the values obtained when the thermoplastic resin fiber (C) was replaced with the thermoplastic resin fiber (B) respectively used in Examples and Comparative Examples. Results are summarized in Tables below.

TABLE 1

|  | Example 1 | Example 2 | Example 3 | Example 4 | Example 5 | Example 6 | Example 7 | Example 8 |
|---|---|---|---|---|---|---|---|---|
| Type of Continuous Reinforcing Fiber (A) | Carbon Fiber | Carbon Fiber | Carbon Fiber | Carbon Fiber | Carbon Fiber | Carbon Fiber | Carbon Fiber | Carbon Fiber |
| Type of Resin b of Continuous Thermoplastic Resin Fiber (B) | MPXD10 | MXD10 | MXD6 | MXD10 | MPXD10 | MPXD10 | MPXD10 | MXD10 |
| Melting Point (° C.) of Resin b | 213 | 190 | 237 | 190 | 213 | 213 | 213 | 190 |
| Fineness of Commingled Yarn (dtex) | 12884 | 12884 | 13814 | 12884 | 13126 | 6553 | 12884 | 12884 |
| Dispersion (%) | 76 | 71 | 80 | 71 | 70 | 78 | 76 | 71 |
| Impregnation Ratio (%) | 0 | 0 | 0 | 0 | 0 | 0 | 0 | 0 |
| Ratio of (A) in Commingled Yarn (wt %) | 62 | 62 | 57 | 62 | 61 | 61 | 62 | 62 |
| Type of Resin c of Thermoplastic Resin Fiber (C) | MPXD6 | MXD6 | MPXD6 | MPXD10 | MPXD6 | MPXD6 | PA66 | MPXD10 |
| Fineness of (C) (dtex) | 122 | 122 | 122 | 129 | 122 | 122 | 123 | 129 |
| Melting Point of Resin c (° C.) | 255 | 237 | 255 | 213 | 255 | 255 | 265 | 213 |
| Melting Point of Resin d that composes Thermoplastic Resin Film (D) | 265 | 265 | 265 | 265 | 265 | 265 | 265 | 265 |
| Melting Point of Resin c – Melting Point of Resin b (° C.) | 42 | 47 | 18 | 23 | 42 | 42 | 52 | 23 |
| Molding Temperature (° C.) | 240 | 220 | 240 | 190 | 240 | 240 | 230 | 195 |
| Post-Heating Temperature (° C.) | — | — | — | — | — | — | — | — |
| Evaluation of Appearance 1 | ◯ | ◯ | ◯ | ◯ | ◯ | ◯ | ◯ | ◯ |
| Evaluation of Appearance 2 | B | B | B | B | B | B | A | B |
| Ratio of Improvement in Mechanical Strength | 4.7 | 4.6 | 4.6 | 4.5 | 4.4 | 4.1 | 3.8 | 3.6 |
| Moldability | ◯ | ◯ | ◯ | ◯ | ◯ | ◯ | ◯ | ◯ |

TABLE 2

|  | Example 9 | Example 10 | Example 11 | Example 12 | Example 13 | Comparative Example 1 |
|---|---|---|---|---|---|---|
| Type of Continuous Reinforcing Fiber (A) | Carbon Fiber | Carbon Fiber | Carbon Fiber | Aramid Fiber | Glass Fiber | Carbon Fiber |
| Type of Resin b of Continuous Thermoplastic Resin Fiber (B) | MPXD10 | MPXD10 | MPXD10 | MPXD10 | MPXD10 | MPXD10 |
| Melting Point (° C.) of Resin b | 213 | 213 | 213 | 213 | 213 | 213 |
| Fineness of Commingled Yarn (dtex) | 12884 | 12884 | 12884 | 11757 | 19012 | 12884 |

TABLE 2-continued

|  | Example 9 | Example 10 | Example 11 | Example 12 | Example 13 | Comparative Example 1 |
|---|---|---|---|---|---|---|
| Dispersion (%) | 76 | 76 | 76 | 76 | 64 | 76 |
| Impregnation Ratio (%) | 9 | 0 | 0 | 0 | 0 | 0 |
| Ratio of (A) in Commingled Yarn (wt %) | 62 | 62 | 62 | 62 | 62 | 62 |
| Type of Resin c of Thermoplastic Resin Fiber (C) | MPXD6 | PA66 | PXD10 | MPXD6 | MPXD6 | MPXD10 |
| Fineness of (C) (dtex) | 122 | 123 | 121 | 121 | 122 | 129 |
| Melting Point of Resin c (° C.) | 255 | 265 | 290 | 255 | 255 | 213 |
| Melting Point of Resin d that composes Thermoplastic Resin Film (D) | 265 | 265 | 265 | 265 | 265 | 265 |
| Melting Point of Resin c – Melting Point of Resin b (° C.) | 42 | 52 | 77 | 42 | 42 | 0 |
| Molding Temperature (° C.) | 240 | 240 | 240 | 240 | 240 | 230 |
| Post-Heating Temperature (° C.) | — | 260 | 275 | — | — | — |
| Evaluation of Appearance 1 | ○ | ○ | ○ | ○ | ○ | x |
| Evaluation of Appearance 2 | B | B | B | B | B | B |
| Ratio of Improvement in Mechanical Strength | 5.1 | 4.9 | 4.8 | 4.1 | 3.2 | 1 |
| Moldability | ○ | ○ | ○ | ○ | ○ | x |

As is clear from the results above, the composite materials of this invention showed almost no disorder of the continuous reinforcing fiber, and found to show large ratios of improvement in the mechanical strength, and good moldability. In contrast, Comparative Example 1 using the same material both for the continuous thermoplastic resin fiber (B) and the thermoplastic resin fiber (C) showed much recognizable disorder of the continuous reinforcing fiber.

<Manufacture of Non-Crimp Fabric>

The commingled yarns used in Example 9 were arranged in parallel as illustrated in FIG. 2(b). That is, a plurality of commingled yarns were arranged in parallel in one direction to form a layer. On the surface thereof, the commingled yarns were arranged in parallel in the direction 90° away from the direction of parallel arrangement of the above-described commingled yarns. A Z-pattern stitching was then given around the commingled yarns using a two-ply fiber of the thermoplastic resin fiber (C) used in Example 9, to thereby obtain a non-crimp fabric of 20 cm wide, with a basis weight of 480 g/m².

<Manufacture of Knee Ankle Foot Orthosis>

The commingled yarns used in Example 1 were stitched on the surface of a polyamide 66 film with an average thickness of 100 μm, patterned so as to correspond with the shape of a knee ankle foot orthosis, using the thermoplastic resin fiber (C) used in Example 1, and the article was then heat-pressed in a die at 240° C., under 2 MPa, for 5 minutes, to obtain the knee ankle foot orthosis.

REFERENCE SIGNS LIST 1 composite material
2, 21 to 25 commingled yarn
31 to 36 layer composed of commingled yarn
C thermoplastic resin fiber (C)
D resin film (D)

The invention claimed is:

1. A composite material comprising:
   a commingled yarn that contains a continuous reinforcing fiber (A) and a continuous thermoplastic resin fiber (B) as fiber components thereof, the continuous reinforcing fiber (A) including carbon fiber and/or glass fiber; and
   a thermoplastic resin fiber (C) that keeps the commingled yarn in place,
   a thermoplastic resin that composes the thermoplastic resin fiber (C) having a melting point 15° C. or more higher than the melting point of a thermoplastic resin that composes the continuous thermoplastic resin fiber (B),
   wherein the commingled yarn is arranged in a base, and is stitched with the thermoplastic resin fiber (C) so as to be kept in place,
   wherein the thermoplastic resin that composes the thermoplastic resin fiber (C) is a polyamide resin, and
   wherein the base is a thermoplastic resin film (D).

2. The composite material of claim 1, wherein the thermoplastic resin that composes the continuous thermoplastic resin fiber (B) is a polyamide resin.

3. The composite material of claim 1, wherein the thermoplastic resin that composes the continuous thermoplastic resin fiber (B) is a polyamide resin that contains a diamine-derived structural unit and a dicarboxylic acid-derived structural unit, 50% by mole or more of the diamine-derived structural unit being derived from xylylenediamine.

4. The composite material of claim 1, wherein a thermoplastic resin that composes the thermoplastic resin film (D) has a melting point 15° C. or more higher than the melting point of the thermoplastic resin that composes the continuous thermoplastic resin fiber (B).

5. The composite material of claim 1, wherein the thermoplastic resin film (D) contains a polyamide resin.

6. The composite material of claim 1, wherein the continuous reinforcing fiber (A) is carbon fiber.

7. The composite material of claim 1, wherein the thermoplastic resin that composes the thermoplastic resin fiber (C) has a melting point 15 to 100° C. higher than the melting point of the thermoplastic resin that composes the continuous thermoplastic resin fiber (B).

8. The composite material of claim 1, wherein the continuous reinforcing fiber (A) in the commingled yarn has a dispersion of 60 to 100%.

9. A composite material comprising:
   a commingled yarn that contains a continuous reinforcing fiber (A) and a continuous thermoplastic resin fiber (B) as fiber components thereof, the continuous reinforcing fiber (A) including carbon fiber and/or glass fiber; and
   a thermoplastic resin fiber (C) that keeps the commingled yarn in place, a thermoplastic resin that composes the thermoplastic resin fiber (C) having a melting point 15° C. or more higher than the melting point of a thermoplastic resin that composes the continuous thermoplastic resin fiber (B), wherein a plurality of commingled yarns are arranged in parallel in one direction to form a first layer; over the first layer of commingled yarn, a plurality of commingled yarns are arranged in parallel to form a second layer, in a direction 10° to 90° away from the parallel direction of the aforementioned commingled yarn of the first layer; and the thermoplastic resin fiber (C) keeps the first layer in place.

10. The composite material of claim 1, wherein the composite material is a non-crimp fabric.

11. The composite material of claim 1, wherein the commingled yarn is bundled by using a treatment agent for at least either one of the continuous reinforcing fiber (A) and the continuous thermoplastic resin fiber (B).

12. The composite material of claim 1, used for manufacturing a medical brace.

13. A method for manufacturing a composite material, the method comprising stitching a base, and a commingled yarn arranged in the base, with a thermoplastic resin fiber (C); the commingled yarn containing, as its fiber components, a continuous reinforcing fiber (A) and a continuous thermoplastic resin fiber (B), the continuous reinforcing fiber (A) including carbon fiber and/or glass fiber; and a thermoplastic resin that composes the thermoplastic resin fiber (C) having a melting point 15° C. or more higher than the melting point of a thermoplastic resin that composes the continuous thermoplastic resin fiber (B), wherein the continuous reinforcing fiber (A) in the commingled yarn has a dispersion of 60 to 100%.

14. A composite material comprising:

a commingled yarn that contains a continuous reinforcing fiber (A) and a continuous thermoplastic resin fiber (B) as fiber components thereof, the continuous reinforcing fiber (A) including carbon fiber and/or glass fiber; and a thermoplastic resin fiber (C) that keeps the commingled yarn in place, a thermoplastic resin that composes the thermoplastic resin fiber (C) having a melting point 15° C. or more higher than the melting point of a thermoplastic resin that composes the continuous thermoplastic resin fiber (B), wherein the thermoplastic resin that composes the continuous thermoplastic resin fiber (B) is a polyamide resin that contains a diamine-derived structural unit and a dicarboxylic acid-derived structural unit, 50% by mole or more of the diamine-derived structural unit being derived from xylylenediamine; and the thermoplastic resin that composes the thermoplastic resin fiber (C) is a polyamide resin, wherein the commingled yarn is arranged in a base and the base is a thermoplastic resin film (D).

15. The composite material of claim 14, wherein the thermoplastic resin that composes the thermoplastic resin fiber (C) has a melting point 15 to 100° C. higher than the melting point of the thermoplastic resin that composes the continuous thermoplastic resin fiber (B).

* * * * *